(12) United States Patent
Puentener et al.

(10) Patent No.: US 7,939,668 B2
(45) Date of Patent: May 10, 2011

(54) RUTHENIUM COMPLEXES AS CATALYSTS FOR METATHESIS REACTIONS

(75) Inventors: Kurt Puentener, Basel (CH);
Michelangelo Scalone, Birsfelden (CH)

(73) Assignee: Roche Palo Alto LLC, South San Francisco, CA (US)

(*) Notice: Subject to any disclaimer, the term of this patent is extended or adjusted under 35 U.S.C. 154(b) by 183 days.

(21) Appl. No.: 12/384,954

(22) Filed: Apr. 10, 2009

(65) Prior Publication Data
US 2009/0275714 A1 Nov. 5, 2009

(30) Foreign Application Priority Data

Apr. 11, 2008 (EP) ..................................... 08154367

(51) Int. Cl.
*C07F 15/00* (2006.01)
*C07C 237/00* (2006.01)
*C07C 59/00* (2006.01)

(52) U.S. Cl. ............ 548/103; 548/403; 548/540; 546/2; 544/64; 544/177; 564/175; 562/471

(58) Field of Classification Search .................. 564/175; 562/471; 548/103, 403, 540; 546/2; 544/64, 544/177
See application file for complete search history.

(56) References Cited

U.S. PATENT DOCUMENTS

| | | | | |
|---|---|---|---|---|
| 2,811,507 A * | 10/1957 | D Alelio | ...................... | 526/304 |
| 5,936,100 A | 8/1999 | Furstner et al. | | |
| 2005/0267018 A1 | 12/2005 | Blatt et al. | | |
| 2006/0063915 A1 | 3/2006 | Gallou et al. | | |

FOREIGN PATENT DOCUMENTS

| | | |
|---|---|---|
| EP | 0921129 A1 | 6/1999 |
| WO | 2004089974 A1 | 10/2004 |
| WO | 2004094452 A2 | 11/2004 |
| WO | 2005016944 A1 | 2/2005 |
| WO | 2008034522 A1 | 3/2008 |

OTHER PUBLICATIONS

Brady et al., Journal of Organic Chemistry, vol. 52, No. 11, pp. 2216-2220 (1987).*
Barrett, A. G. M., et al. "Synthesis of Diverse Macrocyclic Peptidomimetics Utilizing Ring-Closing Metathesis and Solid-Phase Synthesis," The Journal of Organic Chemistry, 2004, vol. 69 (4), pp. 1028-1037.
Bieniek, M. et. al. "In an Attempt to Provide a User's Guide to the Galaxy of Benzylidene, Alkoxybenzylidene, and Indenylidene Ruthenium Olefin Metathesis Catalysts," Chemisty a European Journal, 2008, vol. 14, pp. 806-818.
Brady, W. T., et. al. "Intramolecular [2+2] Cycloadditions of Ketene Iminium Salts to Carbon-Carbon Double Bonds," Journal of Organic Chemistry, 1987, vol. 52, pp. 2216-2220.
Shu, C., et. al. "RCM Macrocyclization Made Practical: An Efficient Synthesis of HCV Protease Inhibitor BILN 2061," Organic Letters, 2008, vol. 10 (6), pp. 1303-1306.

* cited by examiner

*Primary Examiner* — Porfirio Nazario Gonzalez
(74) *Attorney, Agent, or Firm* — Brian L. Buckwalter

(57) ABSTRACT

The invention relates to novel metathesis catalysts of the formula

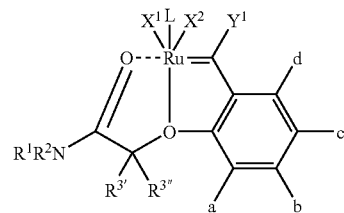

I a process for making the same and their use in metathesis reactions such as ring closing or cross metathesis.
The invention further relates to a process for the manufacture of a macrocyclic compound

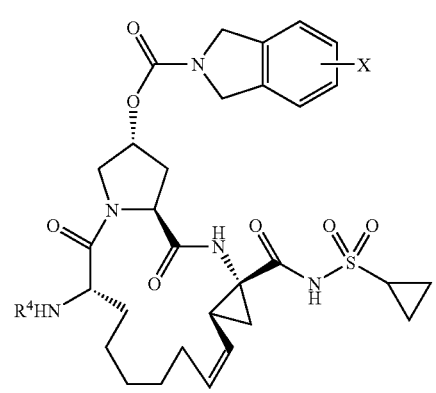

VII of formula VII which have the potential to be useful as HCV protease inhibitors.

36 Claims, 2 Drawing Sheets

RUTHENIUM COMPLEXES AS CATALYSTS FOR METATHESIS REACTIONS

CROSS REFERENCE TO PRIOR APPLICATIONS

This application claims the benefit of priority to EP 08154367.0 filed Apr. 11, 2008 the contents of which are hereby incorporated in their entirety by reference.

FIELD OF THE INVENTION

The present invention relates to novel olefin metathesis catalysts of the formula I and to a process for making the same and their use in metathesis reactions such as ring closing (RCM) or cross metathesis. The invention further relates to a process for the manufacture of a macrocyclic compound of formula VII wherein $R^4$ is an amino protecting group and X is a halogen atom. The invention particularly relates to a process for the manufacture of the HCV protease inhibitor compound of the formula VIII.

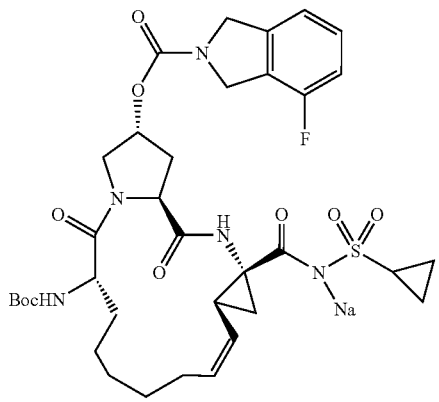

VIII

BACKGROUND OF THE INVENTION

Metathesis reactions catalyzed by ruthenium or other transition metal complexes have been widely applied in the synthesis of macrocyclic compounds. (see, e.g. K. C. Nicolaou et al., *Angew Chem. Int. Ed.* 2005 44:4490-4527). Ring metathesis has been utilized to prepare macrocyclic lactams and peptides. (R. H. Grubbs et al. U.S. Pat. No. 5,811,515; S. F. Martin et al. *Tetrahedron Lett.* 1994 35(5):691-694; B. C. Bennett et al., *Tetrahedron Lett.* 1994 35(19):3191-3194)

In WO 2005/037214 published Apr. 28, 2005 by L. M. Blatt et al. and WO 2007/015824 published Feb. 8, 2007 by S. D. Stewert et al. disclosed the RCM of a diene of the formula 2a the presence of a Nolan or Hoveyda catalyst to form the macrocycle of formula 2b.

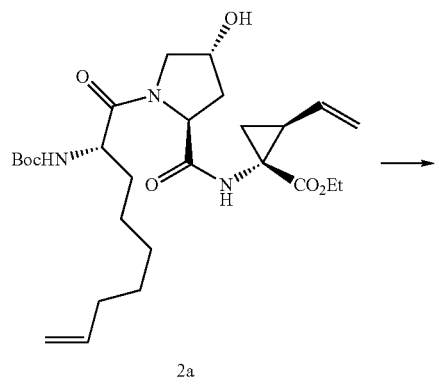

2a

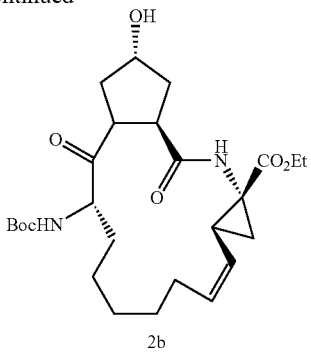

2b

There is a continuing need for improved ring-closing olefin metathesis catalysts to improve the efficiency and to manufacture complex organic molecules which are useful in the treatment of Hepatitis C Virus. (P. H. Deshmukh and S. Blechert, "Alkene Metathesis: the search for better catalysts" *Dalton Trans.* 2007 2479; A. Michrowska and K. Grela, "Quest for the Ideal Metathesis catalyst" *Pure Appl. Chem.* 2008 80(1):31-42)

SUMMARY OF TE INVENTION

The present invention relates to ruthenium (II) complexes according to formula I wherein

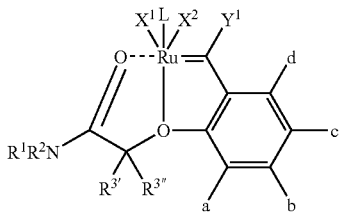

I the dotted line either signifies an optional bond.
L is a neutral ligand.
$X^1$ and $X^2$ independently of each other are anionic ligands.
$Y^1$ is hydrogen, $C_{1-6}$-alkyl, $C_{3-8}$-cycloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, aryloxy, $C_{1-6}$-alkoxycarbonyl, $C_{1-6}$-alkylthio, aryl, arylthio, $C_{1-6}$-alkylsulfonyl or $C_{1-6}$-alkylsulfinyl.
a, b, c and d independently of each other are hydrogen, $C_{1-6}$-alkyl, halogen-$C_{1-6}$-alkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, $SO_3$—$C_{1-6}$-alkyl, $OSi(C_{1-6}$-alkyl$)_3$ or $SO_2$—NR'R" wherein R' and R" are independently hydrogen, aryl or $C_{1-6}$-alkyl or R' and R" together with the N atom form a carbocycle.
$R^1$ and $R^2$ are independently hydrogen, $C_{1-6}$-alkyl, $C_{3-8}$-cycloalkyl, aryl, aryl-$C_{1-6}$-alkyl; or, $R^1$ and $R^2$ together with the N atom to which they are attached form a 5 to 8 member carbocycle which optionally contains a nitrogen, oxygen or sulfur heteroatom.
$R^3$ is hydrogen, $C_{1-6}$-alkyl, $C_{3-8}$-cycloalkyl, aryl, or aryl-$C_{1-6}$-alkyl.

Compounds of formula I are catalysts for ring-closing olefin metathesis (RCM) reactions which provide improved selectivity and efficiency compared to existing catalysts.

An additional aspect of the present invention is a process for the preparation of ruthenium olefin ring-closing metathesis catalysts of formula I.

Another aspect of the present invention is a process for the preparation of macrocyclic compounds of formula V wherein $R^4$ is an amino protecting group, $R^5$ is $C_{1-4}$-alkyl and X is halogen by a ruthenium-catalyzed RCM reaction of the diene IV. Compounds of formula V are useful intermediates for the synthesis of antiviral compounds of formula III. Another aspect of the present invention is a process for converting a compound of formula IV to a compound of formula III. Yet another aspect of the present invention is a process for converting a compound of formula IV to a compound of formula III wherein $R^4$ is a Boc group, X is a 4-fluoro group.

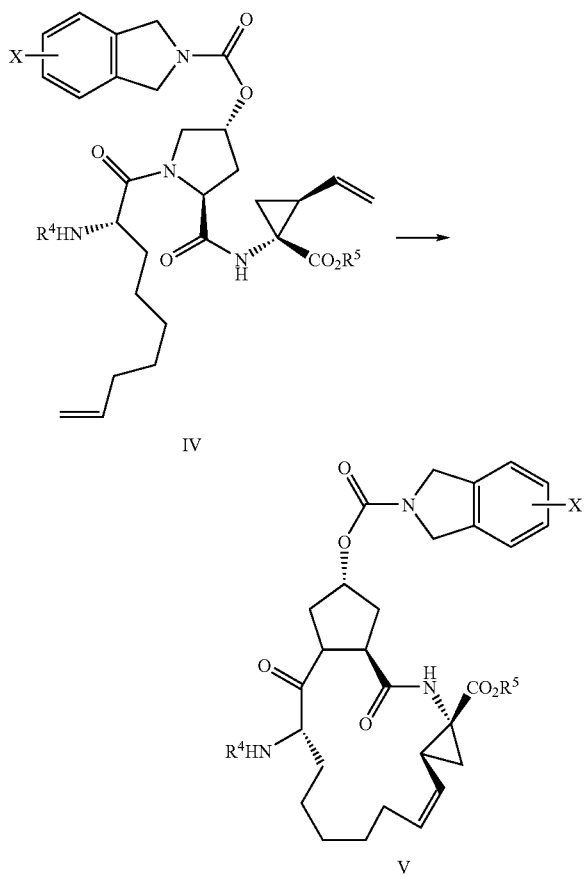

DETAILED DESCRIPTION OF THE INVENTION

Figure 1:
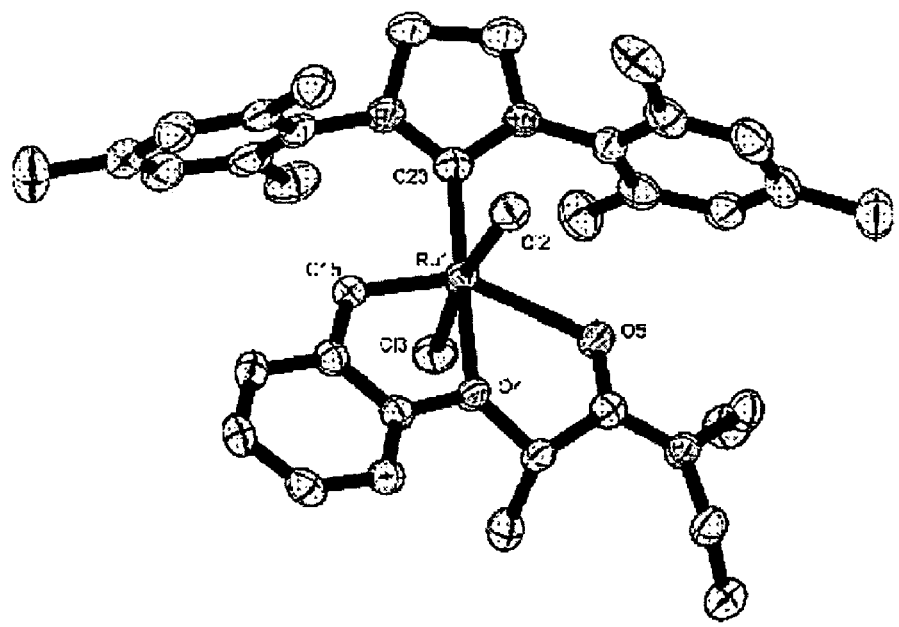
FIG. 1 is an Ortep plot of RuCl$_2$(=CH(o-OCH(Me)CO-NEt$_2$)Ph)(ImH$_2$Mes) (formula D). The collection and the refinement of parameters for the crystallographic analysis are summarized in Table X1 and representative bond lengths and bond angles are reported in Table X2 in the examples section.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "optional bond" means that the bond may or may not be present, and that the description includes single, double, or triple bonds. If a substituent is designated to be a "bond" or "absent", the atoms linked to the substituents are then directly connected.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The RCM methodology disclosed in the art suffers from modest yields and low catalyst selectivity. This translates into low efficiency and higher costs. The object of the present invention therefore was to find superior metathesis catalysts and an improved process that is applicable on technical scale and is able to overcome the disadvantages exhibited by catalysts known in the art. The compounds of formula I can advantageously be used in metathesis reactions, particularly in ring closing metathesis or cross metathesis reactions.

Ru-complexes of formula I wherein $R^1$, $R^2$, $R^{3'}$, $R^{3''}$, $X^1$, $X^2$, $Y^1$, L, a, b, c and d, are as defined herein above and the dotted line is an optional bond, have been found to be very useful catalysts in metathesis reactions such as in ring closing metathesis and in cross metathesis reactions. If the optional bond is absent (i.e. the amide carbonyl group does not coordinate to the ruthenium) the complex is a pentacoordinated ruthenium complex and if the optional bond is present, (i.e. the amide carbonyl group coordinates to the ruthenium) the complex is a hexacoordinated ruthenium complex.

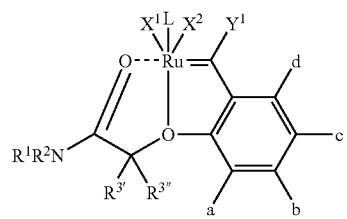

In one embodiment of the present invention there is provided ruthenium ring metathesis catalyst of formula I wherein $R^1$, $R^2$, $R^{3'}$, $R^{3''}$, $X^1$, $X^2$, $Y^1$, L, a, b, c, and d are as defined herein above and the dotted line signifies an optional bond. In another embodiment of the present invention there is provided a compound according to formula I wherein the ruthenium complex is hexacoordinated and $R^1$, $R^2$, $R^{3'}$, $R^{3''}$, $X^1$, $X^2$, $Y^1$, L, a, b, c, and d are as defined herein above.

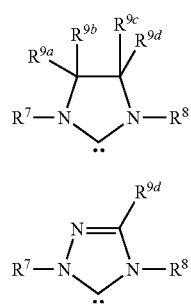

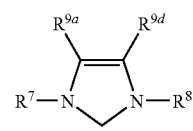

In another embodiment of the present invention there is provided a ruthenium(II) ring metathesis catalysts of formula I wherein $R^1$, $R^2$, $R^{3'}$, $R^{3''}$, $X^1$, $X^2$, $Y^1$, a, b, c, and d are as described herein above; L is IIa, IIb, IIc or IIf; $R^7$ and $R^8$ are independently $C_{1-6}$-alkyl, aryl, $C_{2-6}$-alkenyl or 1-adamantyl and $R^{9a}$, $R^{9b}$, $R^{9c}$ and $R^{9d}$ are independently hydrogen, $C_{1-6}$-alkyl, $C_{2-6}$-alkenyl or aryl, or $R^{9b}$ and $R^{9c}$ or $R^{9a}$ and $R^{9d}$ taken together form a —$(CH_2)_4$- bridge and the Ru (II) complex is hexacoordinated. If L is IIc, $R^{9a}$ and $R^{9d}$ are both halogen, preferably chlorine. If L is IIf and $R^{a1}$, $R^{a2}$ and $R^{a3}$ are independently $C_{1-6}$-alkyl, $C_{3-8}$-cycloalkyl, aryl, heteroaryl or either $R^{a1}$ and $R^{a2}$, $R^{a2}$ and $R^{a3}$ or $R^{a1}$ and $R^{a3}$ taken together form a 1,5-bridged cyclooctyl group. In a more particular embodiments. $R^{a1}$, $R^{a2}$ and $R^{a3}$ are independently cyclohexyl, cyclopentyl, isopropyl and phenyl. Suitable ligands L in formula IIf include, but are not limited to, $Cy_3P$, $iPr_3P$, $Cyp_3P$ or $Ph_3P$ wherein Cy stands for cyclohexyl, Cyp for cyclopentyl and iPr for isopropyl.

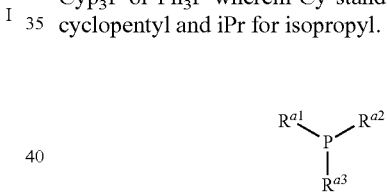

In another embodiment of the present invention there is provided a ruthenium(II) ring metathesis catalysts of formula I wherein $R^1$, $R^2$, $R^{3'}$, $R^{3''}$, $X^1$, $X^2$, $Y^1$, a, b, c, and d are as described herein above; L is L is IId or IIe; and, $R^7$ and $R^8$ are independently $C_{1-6}$-alkyl, aryl, $C_{2-6}$-alkenyl or 1-adamantyl.

In another embodiment there is provided a ruthenium(II) ring metathesis catalysts of formula I wherein $R^1$, $R^2$, $R^{3'}$, $R^{3''}$, $X^1$, $X^2$, $Y^1$, a, b, c, and d are as described herein above; L is L is IId or IIe; and, $R^7$ and $R^8$ are 2,4,6-trimethylphenyl or 2,7-diisopropyl-naphthyl.

In an embodiment of the present invention there is provided a hexacoordinated ruthenium ring metathesis catalysts of formula I wherein $R^1$, $R^2$, $R^{3'}$, $R^{3''}$, $X^1$, $X^2$, $Y^1$, L, a, b, c, and d are as defined herein above; and, $X^1$ and $X^2$ are independently halogen.

In yet another embodiment of the present invention there is provided a hexacoordinated ruthenium ring metathesis catalysts of formula I wherein $R^1$, $R^2$, $R^{3'}$, $R^{3''}$, $X^1$, $X^2$, $Y^1$, L, a, b, c, and d are as defined herein above; and $X^1$ and $X^2$ are chlorine.

In still another embodiment of the present invention there is provided a hexacoordinated ruthenium ring metathesis catalysts of formula I wherein $R^1$, $R^2$, $R^{3'}$, $R^{3''}$, $X^1$, $X^2$, $Y^1$, L, a, b, c, and d are as defined herein above and $Y^1$ is hydrogen.

In an embodiment of the present invention there is provided a hexacoordinated ruthenium ring metathesis catalyst of formula I wherein $R^1$, $R^2$, $R^{3'}$, $R^{3''}$, $X^1$, $X^2$, $Y^1$, L and c, are as defined herein above and a, b and d are hydrogen.

In an embodiment of the present invention there is provided a hexacoordinated ruthenium ring metathesis catalyst of formula I wherein $R^1$, $R^2$, $R^{3'}$, $R^{3''}$, $X^1$, $X^2$, $Y^1$, L, a, b and d are as defined herein above and c is hydrogen, halogen, nitro, $C_{1-6}$-alkylcarbonyl amino, aryl carbonyl amino, aryl sulfonyl amino, alkyl sulfonyl amino, halogen-$C_{1-6}$-alkyl sulfonyl amino, $SO_2NR'R''$ wherein R' and R'' independently of each other have the meaning of hydrogen, $C_{1-6}$-alkyl, aryl or R' and R'' together with the N atom form a carbocycle.

In an embodiment of the present invention there is provided a hexacoordinated ruthenium ring metathesis catalyst of formula I wherein $R^{3'}$, $R^{3''}$, $X^1$, $X^2$, $Y^1$, L, a, b, c, and d are as defined herein above; the ruthenium complex is hexacoordinated; and, $R^1$ and $R^2$ are independently hydrogen, $C_{1-6}$-alkyl or $R^1$ and $R^2$ together with the N atom form a 6 member carbocycle which contains oxygen as additional hetero atom.

In an embodiment of the present invention there is provided a hexacoordinated ruthenium ring metathesis catalyst of formula I wherein $R^1$, $R^2$, $X^1$, $X^2$, $Y^1$, L, a, b, c, and d are as defined herein above; the ruthenium complex is hexacoordinated; and, $R^{3'}$ and $R^{3''}$ are independently hydrogen or $C_{1-6}$ alkyl.

In an embodiment of the present invention there is provided ruthenium ring metathesis catalysts of formula I selected from TABLE I. Preferred complexes comprise complexes D, F, J, L, M and N from TABLE I.

TABLE I

| | | |
|---|---|---|
| D | [structure] | [RuCl$_2$(=CH(o-OCH(Me)CONEt$_2$)Ph)(ImH$_2$Mes)] |
| | Ar = 2,4,6-trimethylphenyl | |
| E | [structure] | [RuCl$_2$(=CH(o-OCH(Me)CONH$_2$)Ph)(ImH$_2$Mes)] |
| | Ar = 2,4,6-trimethylphenyl | |
| F | [structure] | [RuCl$_2$(=CH(o-OCH(Me)CO-N-Morpholine)Ph)(ImH$_2$Mes)] |
| | Ar = 2,4,6-trimethylphenyl | |

TABLE I-continued

| | | |
|---|---|---|
| G | [structure] | [RuCl$_2$(=CH(o-OCH(Me)CONHPh)Ph)(ImH$_2$Mes)] |
| | Ar = 2,4,6-trimethylphenyl | |
| J | [structure] | [RuCl$_2$(=CH(o-OCH(Me)CO-N-Pyrrolidine)Ph)(ImH$_2$Mes)] |
| | Ar = 2,4,6-trimethylphenyl | |
| K | [structure] | [RuCl$_2$(=CH(o-OCH(Me)CO-N-Pyrrolidine)Ph)(PCy$_3$)] |
| | Cy = cyclohexyl | |
| L | [structure] | [RuCl$_2$(=CH(o-OCH(Me)CO-N-Pyrrolidine)Ph)(SIPrNap)] |
| | Naph = 2,7-di-isopropyl-naphth-1 | |
| M | [structure] | [RuCl$_2$(=CH(o-OCMe$_2$CO-N-Pyrrolidine)Ph)(ImH$_2$Mes)] |
| | Ar = 2,4,6-trimethylphenyl | |
| N | [structure] | [RuCl$_2$(=CH(o-OCH$_2$CO-N-Pyrrolidine)Ph)(ImH$_2$Mes)] |
| | Ar = 2,4,6-trimethylphenyl | |

In another embodiment of the present invention there is provided a process for preparing a compound according to formula I by contacting a compound of formula 1.1 with a

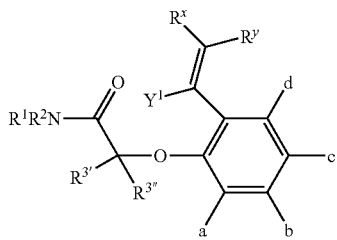

1.1

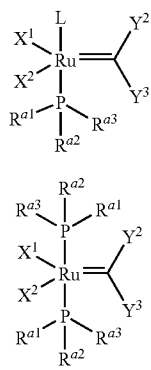

2.1

2.2 ruthenium complex of formula 2.1 or 2.2. The reaction between 1.1 and 2.1 directly affords complexes of formula I. The reaction between 1.1 and 2.2 affords complexes of formula 2.3 which then can be further converted into the compounds of formula I by treatment with ligands L such as IIa, IIb or IIc. The reaction of the compounds of formula 1.1 with ruthenium complexes of formula 2.1 or 2.2 can be performed following the disclosure in PCT Publication WO 2005/0016944.

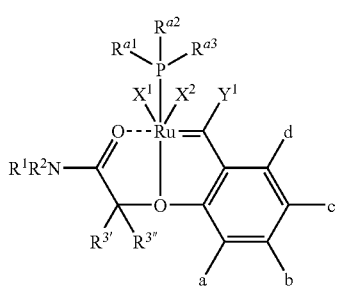

2.3

In the process outlined above the substituents L, $X^1$, $X^2$, $Y^1$, a, b, c, d, $R^1$, $R^2$, $R^{3'}$ and $R^{3''}$ are as defined above. $Y^2$ and $Y^3$ are independently hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl, $C_{1-6}$-alkylsulfinyl; or, $Y^2$ and $Y^3$ taken together are a cycle of formula 3a wherein G is hydrogen or aryl; or, $Y^2$ and $Y^3$ together form a cumulenyl group of formula 3b or 3c.

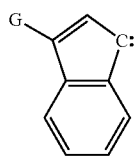

3a

-continued

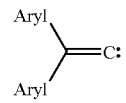

3b

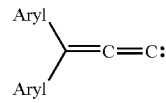

3c $R^x$ and $R^y$ are independently hydrogen, $C_{1-6}$-alkyl optionally substituted by one or more halogen atoms or aryl optionally substituted by one or more halogen atoms or by $C_{1-6}$-alkyl. $R^{a1}$, $R^{a2}$ and $R^{a3}$ are independently $C_{1-6}$-alkyl, $C_{3-8}$-cycloalkyl, aryl, heteroaryl or either $R^{a1}$ and $R^{a2}$ or $R^{a2}$ and $R^{a3}$ or $R^{a1}$ and $R^{a3}$ together form a 1,5-bridged cyclooctyl group.

In another embodiment of the present invention there is provided a process for the preparation of a compound according to formula I wherein the reaction of 1.1 with 2.1 or 2.2 is carried out in an inert solvent at a temperature between 0° C. and 80° C.

In another embodiment of the present invention there is provided a process for the preparation of a compound according to formula I wherein the reaction of 1.1 with 2.1 or 2.2 is carried out in the presence of CuCl.

The compounds of formula 1.1 are novel and thus represent a further embodiment of the present invention. The preferences as outlined above for the compounds of formula I apply also to organic intermediates of formula 1.1 as well.

In another embodiment of the present invention there is provided a compound according to formula 1.1 wherein $R^1$, $R^2$, $R^{3'}$, $R^{3''}$, $Y^1$, a, b, c and d are as described herein above and $R^x$ and $R^y$ are independently hydrogen, $C_{1-6}$-alkyl optionally substituted by one or more halogen atoms or aryl optionally substituted by one or more halogen atoms or by $C_{1-6}$-alkyl.

In another embodiment of the present invention there is provided a compound which can be reacted with compounds of formula 2.1 or 2.2 selected from the group consisting of 1a, 1b, 1c, 1d, 1e, 1f, 1g and 1h.

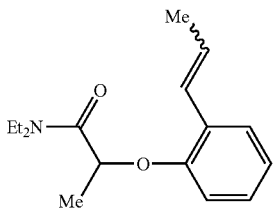

1a

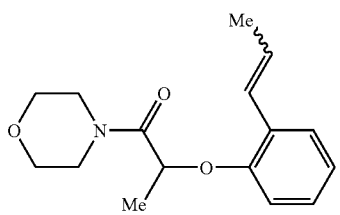

1b

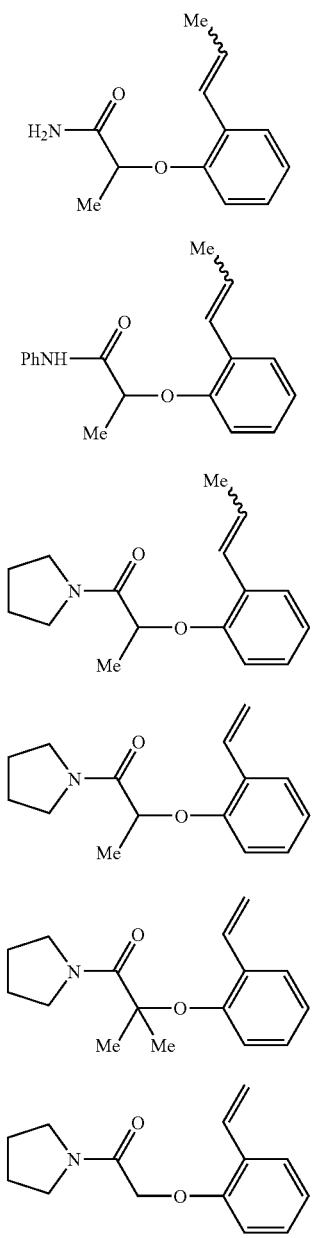

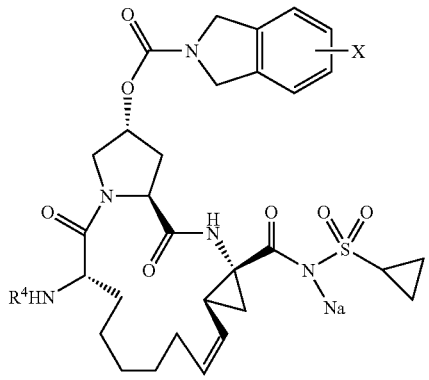

In another embodiment of the present invention there is provided a process for the manufacture of a compound of formula V which is a useful intermediate for the manufacture of compound III which process comprises the step of subjecting a diene

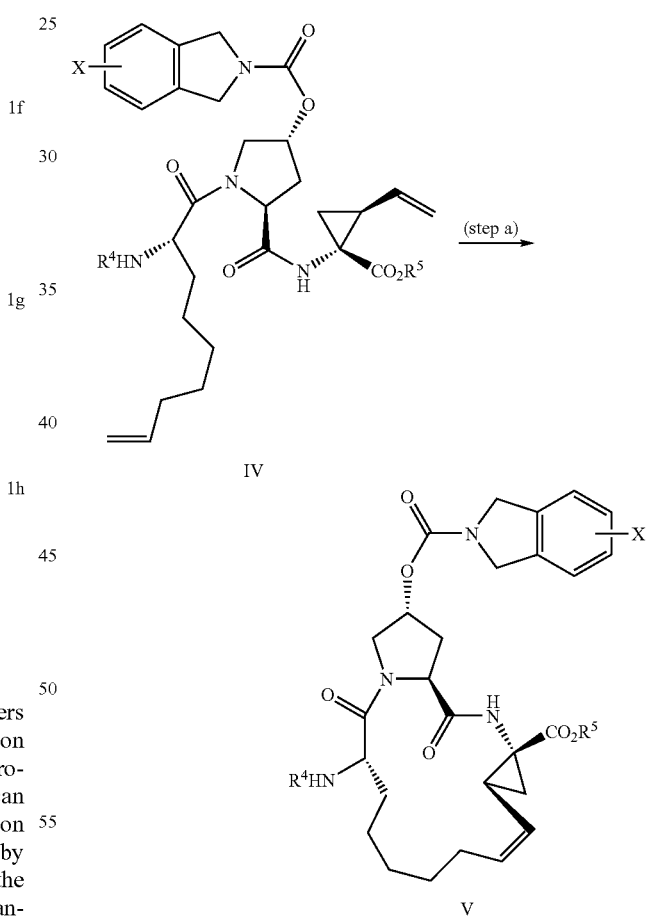

The ligand and complexes can occur as pure enantiomers or mixtures of enantiomers. A suitable solvent for the reaction of 1 with 2 is an inert solvent such as a halogenated hydrocarbon like dichloromethane. The reaction temperature can be chosen between 0° C. and 80° C. The efficiency of ligation of compounds of formula 1a to 1e it can be enhanced by addition of CuCl to the reaction mixture. In this case the reactants are used in equivalent amounts but it can be advantageous to increase the amount of one of the reactants in order to increase the yield.

The compounds of formula I may be separated from other reaction products, e.g. by filtration, and can be purified by chromatography or crystallization. The crude products or the catalyst produced in situ can be used directly to catalyze the RCM reactions.

compound of formula IV wherein $R^4$ is an amino protecting group, $R^5$ is $C_{1-4}$-alkyl and X is halogen to a ring closing metathesis reaction in the presence of a ruthenium (II) carbene complex catalyst to form a macrocyclic ester of the formula V wherein the ruthenium (II) carbene complex catalyst is selected from compounds of the formula Ia, Ib, Ic, Id or Ie:

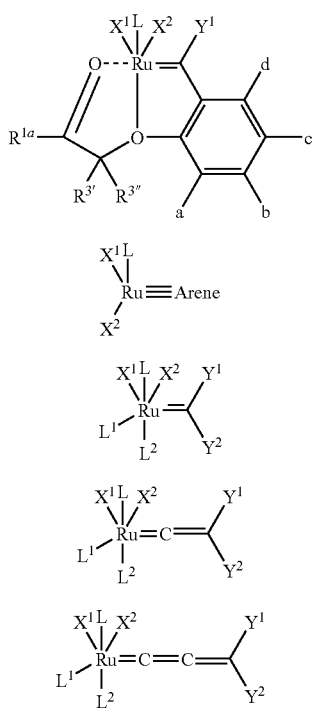

Ia

Ib

Ic

Id

Ie wherein the dotted line represents an optional bond;
L, L$^1$ and L$^2$ are neutral ligands.

X$^1$ and X$^2$ are independently anionic ligands.

Y$^1$ and Y$^2$ are independently hydrogen, C$_{1-6}$-alkyl, C$_{3-8}$-cycloalkyl, C$_{2-6}$-alkenyl, C$_{2-6}$-alkynyl, C$_{1-6}$-alkoxy, C$_{2-6}$-alkenyloxy, C$_{2-6}$-alkynyloxy, aryloxy, C$_{1-6}$-alkoxycarbonyl, C$_{1-6}$-alkylthio, aryl, arylthio, C$_{1-6}$-alkylsulfonyl or C$_{1-6}$-alkylsulfinyl.

a, b, c and d are independently hydrogen, C$_{1-6}$-alkyl, halogen-C$_{1-6}$-alkyl, C$_{2-6}$-alkenyl, C$_{2-6}$-alkynyl, C$_{1-6}$-alkoxy, C$_{2-6}$-alkenyloxy, C$_{2-6}$-alkynyloxy, C$_{1-6}$-alkylcarbonyl, aryl, hydroxy, aryloxy, nitro, C$_{1-6}$-alkoxycarbonyl, amino, mono-C$_{1-6}$-alkyl- or di-C$_{1-6}$-alkylamino, halogen, thio, C$_{1-6}$-alkylthio, arylthio, C$_{1-6}$-alkylsulfonyl, C$_{1-6}$-alkylsulfinyl, arylsulfonyl, SO$_3$H, C$_{1-6}$-alkylcarbonyl amino, aryl carbonyl amino, C$_{1-6}$-alkyl sulfonyl amino, aryl sulfonyl amino, halogen-C$_{1-6}$-alkyl sulfonyl amino, SO$_3$—C$_{1-6}$-alkyl, OSi(C$_{1-6}$-alkyl)$_3$ or SO$_2$—NR'R" wherein R' and R" are independently hydrogen, aryl or C$_{1-6}$-alkyl; or, R' and R" together with the N atom to which they are attached form a carbocycle.

Arene stands for phenyl or naphthyl optionally substituted by one or more substituents selected from the group consisting of halogen, hydroxy, cyano, halogen-C$_{1-6}$-alkyl, NO$_2$, amino, mono-C$_{1-6}$-alkyl- or di-C$_{1-6}$-alkylamino, carboxy, aminocarbonyl, C$_{1-6}$-alkyl, C$_{1-6}$-alkoxy, C$_{1-6}$-alkylcarbonyl, C$_{1-6}$-alkylsulfonyl, aryl, aryloxy SO$_2$-aryl, SO$_3$H, SO$_3$—C$_{1-6}$-alkyl and SO$_2$—NR'R" wherein R' and R" are independently hydrogen or C$_{1-6}$-alkyl.

R$^{1a}$ is hydrogen, hydroxy, C$_{1-6}$-alkoxy, C$_{2-6}$-alkenyloxy, C$_{3-8}$-cycloalkyloxy, halogen, C$_{1-6}$-alkyloxy, aryloxy, C$_{1-6}$-alkylthio, arylthio, or —NR'R" wherein R' and R" are independently hydrogen, C$_{1-6}$-alkyl, C$_{3-8}$-cycloalkyl, aryl, aryl-C$_{1-6}$-alkyl or wherein R' and R" together with the N atom to which they are attached form a 5 to 8 member carbocycle optionally containing a nitrogen, oxygen or sulfur hetero atom.

R$^3$ and R$^{3'''}$ are independently H, C$_{1-6}$-alkyl, C$_{3-8}$-cycloalkyl, aryl or C$_{7-18}$-arylalkyl; or, R$^{1a}$ and R$^3$ together form a 5 to 12 member carbocycle.

In a another embodiment of the present invention there is provided a process for the manufacture of a compound of formula V wherein the ruthenium (II) carbene complex is selected from compounds Ia, Ib or Ic and R$^{1a}$, R$^{3'}$, R$^{3'''}$, L, L$^1$, L$^2$, X$^1$, X$^2$, Y$^1$, Y$^2$ a, b, c and d are as defined here and above.

In another embodiment of the invention the ruthenium (II) carbene complex is selected from compounds Ia, Ib or Ic wherein L, L$^1$ and L$^2$ are the same or different and that at least L is a N-heterocyclic carbene ligand and R$^{1a}$, R$^{3'}$, R$^{3'''}$, L, L$^1$, L$^2$, X$^1$, X$^2$, Y$^1$, Y$^2$ a, b, c and d are as defined here and above.

In another embodiment of the present invention there is provided a process wherein the ruthenium (II) carbene complex is selected from compounds Ia and R$^{1a}$, R$^{3'}$, R$^{3'''}$, L, X$^1$, X$^2$, Y$^1$, a, b, c and d are as defined here and above.

In yet another embodiment of the invention the ruthenium (II) carbene complex is selected from compounds Ia wherein L is a N-heterocyclic carbene ligand selected from IIa, IIb and Ic wherein R$^7$ and R$^8$ independently of each other are C$_{1-6}$-alkyl, aryl, C$_{2-6}$-alkenyl or 1-adamantyl and R$^{9a-d}$ are independently of each other hydrogen, C$_{1-6}$-alkyl, C$_{2-6}$-alkenyl or aryl, or R$^{9b}$ and R$^{9c}$ or R$^{9a}$ and R$^{9d}$ taken together form a —(CH$_2$)$_4$-bridge and R$^{1a}$, R$^{3'}$, R$^{3'''}$, L, L$^1$, L$^2$, X$^1$, X$^2$, Y$^1$, Y$^2$ a, b, c and d are as defined here and above.

In another preferred embodiment of the present invention there is provided a process wherein the ruthenium (II) carbene complex is selected from compounds Ia, Ib or Ic wherein L is selected from IIa, IIb or IIc wherein R$^7$ and R$^8$ independently of each other are C$_{1-6}$-alkyl, aryl, C$_{2-6}$-alkenyl or 1-adamantyl and R$^{9a-d}$ are independently of each other hydrogen, C$_{1-6}$-alkyl, C$_{2-6}$-alkenyl or aryl, or R$^{9b}$ and R$^{9c}$ or R$^{9a}$ and R$^{9d}$ taken together form a —(CH$_2$)$_4$-bridge and R$^{1a}$, R$^{3'}$, R$^{3'''}$, L, L$^1$, L$^2$, X$^1$, X$^2$, Y$^1$, Y$^2$ a, b, c and d are as defined here and above.

In another embodiment of the present invention there is provided a process wherein the ruthenium (II) carbene complex is selected from compounds Ia, Ib or Ic wherein X$^1$ and X$^2$ are independently halogen and R$^{1a}$, R$^{3'}$, R$^{3'''}$, L, L$^1$, L$^2$, Y$^1$, Y$^2$ a, b, c and d are as defined here and above.

In another embodiment of the present invention there is provided a process wherein the ruthenium (II) carbene complex is selected from compounds Ia or Ic wherein Y$^1$ and Y$^2$ are independently hydrogen, C$_{1-6}$ alkyl, aryl or arylthio and R$^{1a}$, R$^{3'}$, R$^{3'''}$, L, L$^1$, L$^2$, X$^1$, X$^2$, a, b, c and d are as defined here and above.

In another embodiment of the present invention there is provided a process wherein the ruthenium (II) carbene complex is Ia, a, b and d are hydrogen as defined here and above.

In a another embodiment of the present invention there is provided a process wherein the ruthenium (II) carbene complex is Ia and c is hydrogen, halogen, nitro, C$_{1-6}$-alkylcarbonyl amino, aryl carbonyl amino, aryl sulfonyl amino, alkyl sulfonyl amino, halogen-C$_{1-6}$-alkyl sulfonyl amino or SO$_2$—NR'R" wherein R' and R" independently of each other have the meaning of hydrogen, C$_{1-6}$-alkyl, aryl or wherein R' and R" together with the N atom form a cycle.

In another embodiment of the present invention there is provided a process wherein the ruthenium (II) carbene complex of formula I is D, F or J.

In another embodiment of the present invention there is provided a process wherein the ruthenium (II) carbene complex is Ib and Arene is benzene, p-cymene, mesitylene orp-xylene and X$^1$, X$^2$ L are as defined here and above.

In another embodiment of the present invention there is provided a process wherein the ring closing metathesis reaction is performed in an organic solvent at 20° C. to 140° C.

In another embodiment of the present invention there is provided a process wherein ratio of substrate to catalyst in the ring closing metathesis reaction is 20 to 10,000.

In another embodiment of the present invention there is provided a process for the manufacture of a macrocyclic compound of formula III which comprises the ring closure as described above (step a) and which process further comprises the steps of (step b) hydrolyzing the macrocyclic ester of formula V in the presence of a base to form the macrocyclic acid of the formula VI wherein $R^4$ is an amino protecting group and X is halogen; and (step c) contacting VI with cyclopropylsulfonamide to produce the macrocyclic sulfonamide of formula VII; and, (step d) treating the macrocyclic sulfonamide of formula VII with a sodium base.

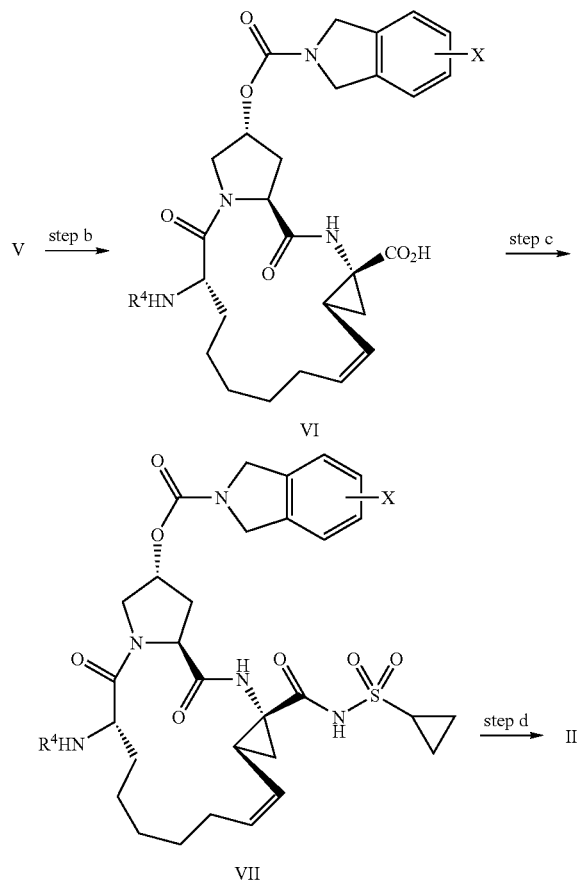

In an embodiment of the present invention there is provided a process for the manufacture of a compound of formula III wherein $R^4$ is an amine protecting group and X is a halogen atom, comprising the steps of (a)-(d) wherein in step (b) the macrocyclic acid of formula VI obtained in step (b) is isolated by way of extraction with dichloromethane and a subsequent crystallization in tetrahydrofuran.

In an embodiment of the present invention there is provided a process for the manufacture of a compound of formula III wherein $R^4$ is an amine protecting group and X is a halogen atom, comprising the steps of (a)-(d) wherein step (c) further comprises initially contacting the macrocyclic acid of formula VI with acetic acid anhydride in the presence of an inorganic base

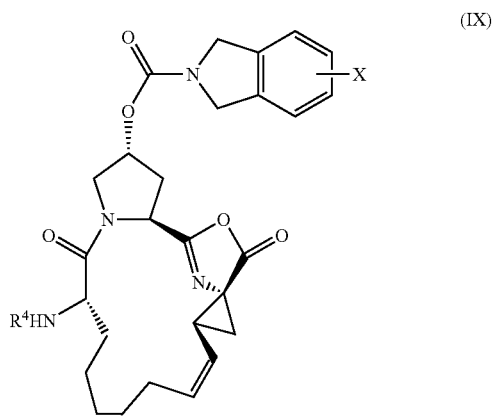

and a suitable organic solvent to produce the azlacton IX wherein $R^4$ is an amino protecting group and X is halogen and further contacting IX with cyclopropyl sulfonamide in the presence of an inorganic base to the macrocyclic sulfonamide to afford VII.

In an embodiment of the present invention there is provided a process for the manufacture of a compound of formula III wherein $R^4$ is an amine protecting group and X is a halogen atom, comprising the steps of (a)-(d) wherein step (d) the sodium base is sodium hydroxide, sodium methylate or sodium ethoxide.

In an embodiment of the present invention there is provided a process for the manufacture of a compound of formula III wherein $R^4$ is an amine protecting group and X is a halogen atom, comprising the steps of (a)-(d) wherein $R^4$ is Boc; $R^5$ is ethyl and the halogen substituted 2,3-dihydro-1H-isoindole moiety is 4-fluoro-2,3-dihydro-1H-isoindole.

The following definitions are set forth to illustrate and define the meaning and scope of the various terms used to describe the invention herein.

The term "amino protecting group" refers to any substituents conventionally used to hinder the reactivity of the amino group. Suitable amino protecting groups are described in T. Green, "Protective Groups in Organic Synthesis", Chapter 7, John Wiley and Sons, Inc., 1991, 309-385. Suitable amino protecting groups include Fmoc, Cbz, Moz, Boc, Troc, Teoc or Voc. A preferred amino protecting group as defined for $R^4$ is Boc.

The term "halogen" refers to fluorine, chlorine, bromine and iodine. The preferred halogen for X is fluorine and for $X^1$ and $X^2$ is chlorine.

In one embodiment the moiety of the formula (I) is 4-fluoro-2,3-dihydro-1H-isoindole (ii)

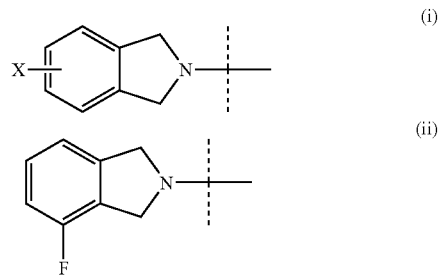

The term "$C_{1-6}$-alkyl", alone or in combination with other groups, refers to a branched or straight-chain monovalent saturated aliphatic hydrocarbon radical of one to six carbon atoms, preferably one to four carbon atoms. This term is further exemplified by radicals as methyl, ethyl, n-propyl, isopropyl, n-butyl, s-butyl, t-butyl and pentyl or hexyl and its isomers.

The term "$C_{1-4}$-alkyl" as used in herein for $R^5$ refers to a branched or straight-chain monovalent saturated aliphatic hydrocarbon radical of one to four carbon atoms such as methyl, ethyl, n-propyl, isopropyl, n-butyl, s-butyl, t-butyl, preferably to ethyl.

The term "$C_{2-6}$-alkenyl", alone or in combination with other groups, refers to a branched or straight-chain monovalent unsaturated aliphatic hydrocarbon radical of two to six carbon atoms, preferably two to four carbon atoms. This term is further exemplified by radicals such as vinyl, propenyl, butenyl, pentenyl and hexenyl and their isomers. A preferred alkenyl radical is vinyl.

The term "$C_{2-6}$-alkynyl", alone or in combination with other groups, refers to a branched or straight-chain monovalent unsaturated aliphatic hydrocarbon radical of two to six carbon atoms, preferably two to four carbon atoms. This term is further exemplified by radicals such as ethynyl, propynyl, butynyl, pentynyl or hexynyl their isomers.

The term "halogen-$C_{1-6}$-alkyl" refers to a halogen substituted $C_{1-6}$-alkyl radical wherein halogen is as defined above. Preferred "halogen-$C_{1-6}$-alkyl" radicals are the fluorinated $C_{1-6}$-alkyl radicals such as $CF_3$, $CH_2CF_3$, $CH(CF_3)_2$, $CH(CH_3)(CF_3)$, $C_4F_9$.

The term "$C_{1-6}$-alkoxy" refers to a branched or straight-chain monovalent saturated aliphatic hydrocarbon radical of one to six carbon atoms, preferably 1 to 4 carbon atoms attached to an oxygen atom. Examples of "alkoxy" are methoxy, ethoxy, propoxy, isopropoxy, butoxy, isobutoxy and hexyloxy. The alkyl chain of the alkoxy group can optionally be substituted, particularly mono-, di- or tri-substituted by alkoxy groups as defined above, preferably methoxy, or ethoxy or by aryl groups, preferably phenyl. A preferred substituted alkoxy group is the benzyloxy group.

The term "$C_{1-6}$-alkyl carbonyl" refers to $C_{1-6}$-alkyl substituted carbonyl group, preferably to a $C_{1-4}$-alkycarbonyl group. It includes for example acetyl, propanoyl, butanoyl or pivaloyl. A preferred alkyl carbonyl group is acetyl.

The term "$C_{1-6}$-alkylthio" refers to the group $C_{1-6}$-alkyl-S—, preferably $C_{1-4}$-alkyl e.g., methylthio or ethylthio.

The term "arylthio" refers to a group aryl-S—, preferably to phenylthio.

The term "$C_{1-6}$-alkylsulfonyl" refers to a $C_{1-6}$-alkyl substituted sulfonyl group, preferably to methylsulfonyl.

The term "$C_{1-6}$-alkylsulfinyl" refers to a $C_{1-6}$-alkyl substituted sulfinyl group, preferably to methylsulfinyl.

The term "$SO_2$-aryl" refers to a sulfonyl substituted aryl radical. A preferred $SO_2$-aryl radical is $SO_2$-phenyl.

The term "$SO_2$—NR'R'" refers to a sulfonyl group substituted with an amino group NR'R' wherein R' and R" are independently hydrogen or $C_{1-6}$-alkyl; or, R' and R" is together with the N atom to which they are attached form a carbocycle, e.g. —$(CH_2)_4$— or —$(CH)_4$—. A preferred $SO_2$—NR'R" radical is $SO_2$—$N(CH_3)_2$.

The term "mono- or di-$C_{1-6}$-alkyl-amino" refers to an amino group, which is mono- or disubstituted with $C_{1-6}$-alkyl, preferably $C_{1-4}$-alkyl. A mono-$C_{1-6}$-alkyl-amino group includes for example methylamino or ethylamino. The term "di-$C_{1-6}$-alkyl-amino" includes for example dimethylamino, diethylamino or ethylmethylamino. Preferred are the mono- or di-$C_{1-4}$-alkylamino groups specifically exemplified herein. It is hereby understood that the term "di-$C_{1-6}$-alkyl-amino" includes ring systems wherein the two alkyl groups together with the nitrogen atom to which they are attached form a 4 to 7 membered heterocycle which also may optionally contain a additional heteroatom selected from nitrogen, oxygen and sulfur.

The term "cycloalkyl" denotes a "$C_{3-8}$-cycloalkyl" group containing from 3 to 8 carbon atoms, such as cyclopropyl, cyclobutyl, cyclopentyl, cyclohexyl, cycloheptyl or cyclooctyl.

The term "aryl" relates to the phenyl or naphthyl group, preferably the phenyl group, which can optionally be mono-, di-, tri- or multiply-substituted by halogen, hydroxy, CN, halogen-$C_{1-6}$-alkyl, $NO_2$, $NH_2$, NH(alkyl), N(alkyl)$_2$, carboxy, aminocarbonyl, alkyl, alkoxy, alkylcarbonyl, $C_{1-6}$-alkylsulfonyl, $SO_2$-aryl, $SO_3H$, $SO_3$-alkyl, $SO_2$—NR'R", aryl and/or aryloxy. Multiple substituents on the aryl ring are independently selected from the above list. A preferred aryl group is phenyl.

The term "aryloxy" relates to an aryl radical attached to an oxygen atom. The term "aryl" has the meaning as defined above. Preferred aryloxy group is phenyloxy.

The term "arylalkyl" relates to an aryl radical attached to an alkyl group. The term "aryl" has the meaning as defined above. Preferred arylalkyl group is benzyl.

The term "heteroaryl" relates to an aryl radical containing 1 to 3 heteroatoms in the ring with the remainder being carbon atoms. Suitable heteroatoms include, without limitation, oxygen, sulfur, and nitrogen. Exemplary heteroaryl groups include furanyl, thienyl, pyridyl, pyrrolyl, N-alkyl pyrrolo, pyrimidyl, pyrazinyl, imidazolyl, benzofuranyl, quinolinyl, and indolyl. Like the aryl group the heteroaryl group can optionally be mono-, di-, tri- or multiply-substituted by halogen, hydroxy, CN, $NO_2$, $NH_2$, NH(alkyl), N(alkyl)$_2$, carboxy, aminocarbonyl, alkyl, alkoxy, alkylcarbonyl, $C_{1-6}$-alkylsulfonyl, $SO_2$-aryl, $SO_3H$, $SO_3$-alkyl, $SO_2$—NR'R", aryl and/or aryloxy. Multiple substituents on the heteroaryl ring are independently selected from the above list.

The compounds of formula I can preferably be characterized by the following definitions.

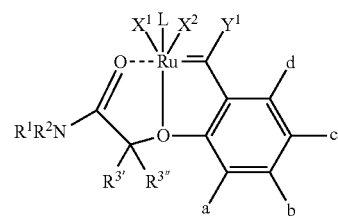

I

Compounds of formula I wherein the dotted line represents the absence of a bond (i.e., there is no coordination between the amide carbonyl group to the ruthenium (II) atom) results in a pentacoordinated ruthenium complex.

Compounds of formula I wherein the dotted line represents a bond (i.e. the amide carbonyl group coordinates to ruthenium (II)) resulting in a hexacoordinated ruthenium complex are preferred.

The ligand L is a neutral ligand can be selected from IIa, IIb or IIc wherein $R^7$ and $R^8$ independently of each other are $C_{1-6}$-alkyl, aryl, $C_{2-6}$-alkenyl or 1-adamantyl and $R^{9a-d}$ are independently of each other hydrogen, $C_{1-6}$-alkyl, $C_{2-6}$-alkenyl or aryl, or $R^{9b}$ and $R^{9c}$ or $R^{9a}$ and $R^{9d}$ taken together form a —$(CH_2)_4$-bridge.

In an embodiment $R^7$ and $R^8$ are $C_{1-6}$-alkyl or a phenyl group which is di- or tri-substituted with $C_{1-6}$-alkyl. In one embodiment $R^7$ and $R^8$ more are t-butyl, 1-adamantyl, isopropyl, 2,6-diisopropylphenyl or 2,4,6-trimethylphenyl most preferably 2,4,6-trimethylphenyl.

In another embodiment $R^{9a}$ and $R^{9c}$ are methyl or phenyl and $R^{9b}$ and $R^{9d}$ are hydrogen, or $R^{9a}$ and $R^{9c}$ or $R^{9b}$ and $R^{9d}$ are taken together to form a —$(CH_2)_n$-bridge with n having the meaning of 5 or 6. Its herby understood that if chiral carbon atoms are present, both the racemic and the enantiomericaHy pure form are comprised. In a further embodiment $R^{9a-d}$ are hydrogen.

In yet another embodiment L is IId or IIe wherein $R^7$ and $R^8$ are $C_{1-6}$-alkyl or a phenyl group which is di- or tri-substituted with $C_{1-6}$-alkyl. In still another embodiment $R^7$ and $R^8$ are t-butyl, 1-adamantyl, isopropyl, 2,6-diisopropylphenyl or 2,4,6-trimethylphenyl and in still another embodiment $R^7$ and $R^8$ are 2,4,6-trimethylphenyl.

$X^1$ and $X^2$ are independently a halogenide or a pseudo halogenide such as cyanide, a rhodanide, a cyanate, an isocycanate, acetate or trifluoroacetate may be selected. In an embodiment of the present invention anionic ligands $X^1$ and $X^2$ are a halogenide. In another embodiment of the present invention $X^1$ and $X^2$ are chloro.

In one embodiment of the present invention $Y^1$ is hydrogen.

In another embodiment of the present invention a, b and d are hydrogen.

In another embodiment of the present invention c is hydrogen, halogen, nitro, $C_{1-6}$-alkylcarbonyl amino, aryl carbonyl amino, aryl sulfonyl amino, alkyl sulfonyl amino, halogen-$C_{1-6}$-alkyl sulfonyl amino, $SO_2$—NR'R" wherein R' and R" independently of each other have the meaning of hydrogen, $C_{1-6}$-alkyl, aryl or R' and R" together with the N atom form a carbocycle. In yet another embodiment of the present invention c means hydrogen, Cl, nitro, $SO_2$—NR'R".

In another embodiment of the present invention $R^1$ and $R^2$ independently of each other are hydrogen, $C_{1-6}$-alkyl or $R^1$ and $R^2$ together with the N atom form a 6 member carbocycle which contains oxygen as additional hetero atom. In yet another embodiment of the present invention $R^1$ and $R^2$ independently of each other are hydrogen or $C_{1-6}$-alkyl.

In embodiment of the present invention $R^3$ is hydrogen or $C_{1-6}$-alkyl. In another embodiment of the present invention $R^3$ is methyl.

In an embodiment of the present invention there is provided a ruthenium (II) RCM catalyst selected from TABLE I (supra). In still another embodiment of the present invention there is provided a ruthenium (II) RCM catalyst selected from examples D, F, J, L, M and N in TABLE I.

For the determination of the hexacoordination crystals of complex D suitable for X-ray crystal structure analysis were grown by vapor diffusion of pentane into a saturated tetrahydrofuran solution at room temperature. For the determination of the hexacoordination crystals of complex F suitable for X-ray crystal structure analysis were grown by vapor diffusion of pentane into a saturated dichloromethane solution at room temperature. For the determination of the pentacoordination crystals of complex E suitable for X-ray crystal structure analysis were grown by vapor diffusion of pentane into a saturated tetrahydrofuran solution at room temperature.

Step (a)

Step (a) requires the transformation of the diene compound of formula IV via RCM reaction into the macrocyclic ester of formula V.

In one embodiment of the present process the RCM reaction is advantageously performed with a ruthenium (II) carbene complex catalyst selected from compounds of the formula Ia, Ib, Ic, Id or Ie wherein:

the dotted line either signifies the existence of a bond or absence of a bond;

L, $L^1$ and $L^2$ are neutral ligands;

$X^1$ and $X^2$ independently of each other are anionic ligands;

$Y^1$ and $Y^2$ independently of each other is hydrogen, $C_{1-6}$-alkyl, $C_{3-8}$-cycloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, aryloxy, $C_{1-6}$-alkoxycarbonyl, $C_{1-6}$-alaylthio, aryl, arylthio, $C_{1-6}$-alylsulfonyl, $C_{1-6}$-alkylsulfnyl;

a, b, c and d independently of each other have the meaning of hydrogen, $C_{1-6}$-alkyl, halogen-$C_{1-6}$-alkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, halogen-$C_{1-4}$-alkyl sulfonyl amino, $SO_3$—$C_{1-6}$-alkyl or $OSi(C_{1-6}$-alkyl$)_3$ and $SO_2$—NR'R" wherein R' and R" independently of each other have the meaning of hydrogen, aryl or $C_{1-6}$-alkyl or R' and R" together with the N atom form a carbocycle;

Arene stands for phenyl or naphthyl optionally mono-, di-, tri- or multiply-substituted by halogen, hydroxy, cyano, halogen-$C_{1-6}$-alkyl, $NO_2$, amino, mono-$C_{1-6}$-alkyl- or di-$C_{1-6}$-alkylamino, carboxy, aminocarbonyl, $C_{1-6}$-alkyl, $C_{1-6}$-alkoxy, $C_{1-6}$-alkylcarbonyl, $C_{1-6}$-alkylsulfonyl, aryl, aryloxy $SO_2$-aryl, $SO_3H$, $SO_3$—$C_{1-6}$-alkyl, $SO_2$—NR'R" wherein R' and R" independently of each other are hydrogen or $C_{1-6}$-alkyl;

$R^{1a}$ is hydrogen, hydroxy, $C_{1-6}$-alkoxy, $C_{2-6}$-alkenyloxy, $C_{3-8}$-cycloalkyloxy, halogen-$C_{1-6}$-alkyloxy, aryloxy, $C_{1-6}$-alkylthio, arylthio, or —NR'R" wherein R' and R" independently of each other are hydrogen, $C_{1-6}$-alkyl, $C_{3-8}$-cycloalkyl, aryl, aryl-$C_{1-6}$-alkyl or wherein R' and R" together with the N atom form a 5 to 8 member carbocycle which may contain nitrogen, oxygen or sulfur as additional hetero atom;

$R^3$ and $R^{3''}$ are independently hydrogen, $C_{1-6}$-alkyl, $C_{3-8}$-cycloalkyl, aryl, $C_{7-18}$-arylalkyl or $R^{1a}$ and $R^3$ together form a 5 to 12 member carbocycle.

In another embodiment of the present process the RCM reaction is advantageously performed with a ruthenium (II) carbene complex catalyst selected from compounds of the formula Ia, Ib or Ic. In another embodiment of the present process the RCM reaction is advantageously performed with a ruthenium (II) carbene complex catalyst of the formula Ia.

In another embodiment of the present process the RCM reaction is advantageously performed with a ruthenium (II) carbene complex catalyst wherein L, $L^1$ and $L^2$ are the same or different and at least one of L, $L^1$ and $L^2$ is a N-heterocyclic carbene ligand selected from IIa, IIb or IIc wherein $R^7$ and $R^8$ are independently $C_{1-6}$-alkyl, aryl, $C_{2-6}$-alkenyl or 1-adamantyl and $R^{9a-d}$ are independently of each other hydrogen, $C_{1-6}$-alkyl, $C_{2-6}$-alkenyl or aryl, or $R^{9b}$ and $R^{9c}$ or $R^{9a}$ and $R^{9d}$ taken together form a —$(CH_2)_4$-bridge.

In another embodiment of the present process the RCM reaction is advantageously performed with a ruthenium (II) carbene complex catalyst wherein $R^7$ and $R^8$ are selected from t-butyl, 1-adamantyl, isopropyl, 2,6-diisopropylphenyl or 2,4,6-trimethylphenyl. In yet another embodiment of the present process the RCM reaction is advantageously performed with a ruthenium (II) carbene complex catalyst wherein $R^7$ and $R^8$ are 2,4,6-trimethylphenyl.

In another embodiment of the present process the RCM reaction is advantageously performed with a ruthenium (II) carbene complex catalyst wherein $R^{9a-d}$ is hydrogen and L is IId or IIe wherein $R^7$ and $R^8$ are as described above.

In another embodiment of the present process the RCM reaction is advantageously performed with a ruthenium (II) carbene complex catalyst wherein $L^1$ and $L^2$ independently of each other are preferably selected from N-heteroaryl, particularly pyridyl which can optionally be substituted with the substituents as defined above for heteroaryl.

In another embodiment of the present process the RCM reaction is advantageously performed with a ruthenium (II) carbene complex catalyst wherein $X^1$ and $X^2$ are independently halogen, preferably chlorine.

In another embodiment of the present process the RCM reaction is advantageously performed with a ruthenium (II) carbene complex catalyst wherein $Y^1$ and $Y^2$ independently of each other preferably are hydrogen, $C_{1-6}$-alkyl, aryl or arylthio, In another embodiment of the present process the RCM reaction is advantageously performed with a ruthenium (II) carbene complex catalyst of formula Ia wherein a, b and d are hydrogen and c is hydrogen, halogen, nitro, $C_{1-6}$-alkylcarbonyl amino, aryl carbonyl amino, aryl sulfonyl amino, alkyl sulfonyl amino, halogen-$C_1$-alkryl sulfonyl amino, $SO_2$—NR'R" wherein R' and R" independently of each other have the meaning of hydrogen, $C_{1-6}$-alkyl, aryl or wherein R' and R" together with the N atom form a carbocycle.

In another embodiment of the present process the RCM reaction is advantageously performed with a ruthenium (II) carbene complex catalyst of formula Ib wherein Arene is benzene, p-cymene, mesitylene or, p-xylene. In yet another embodiment Arene is p-cymene.

In another embodiment of the present process the RCM reaction is advantageously performed with a ruthenium (II) carbene complex catalyst selected from TABLE I (supra). In yet another embodiment of the present process the RCM reaction is advantageously performed with a ruthenium (II) carbene complex catalyst selected compounds D, F, J, M, L and N in TABLE I. In still another embodiment of the present process the RCM reaction is advantageously performed with a ruthenium (II) carbene complex catalyst selected compounds D, F and J in TABLE I.

The RCM reaction is usually performed in an organic solvent, preferably in an aromatic organic solvent such as in benzene, toluene or mesitylene or in halogenated aromatic solvents such as in polyfluorinated benzenes or toluenes. Also halogenated hydrocarbons such as dichloromethane or dichloroethane are suitable solvents. The solvents may be used as single solvent or as a mixture of different solvents. In addition a co-solvent selected from an aliphatic hydrocarbon such as pentane, hexane or heptane may be used as well.

The reaction temperature is selected in a range of 20° C. to 140° C., preferably 40° C. to 100° C. and even more preferred 50° C. to 90° C.

The molar substrate to catalyst ratio S/C is usually selected in a range of 20 to 10000, but preferably in a range of 200 to 4000. It is convenient to run the reaction either under bubbling of an inert gas through the reaction mixture or under a slight vacuum.

The macrocyclic ester of formula I can be isolated by applying methods known to the skilled in the art such as by column chromatography or by crystallisation. The metathesis reaction mixture can also, after a simple extractive work-up, be brought directly into the next step.

In order to remove most catalyst from the solution of the macrocyclic ester it is convenient to treat the reaction mixture with a complexing agent such as ethylenediamine and to extract the resulting soluble ruthenium species into acidic water. The amount of ethylenediamine is not critical; it can be used in a 1:1 to 100:1 molar ratio relative to the catalyst, preferentially in 20:1 to 70:1 molar ratio.

Step (b)

Step b is the hydrolysis of the macrocyclic ester of formula V to afford the macrocyclic acid of formula VI.

In a one embodiment the macrocyclic ester of the formula Vb is used.

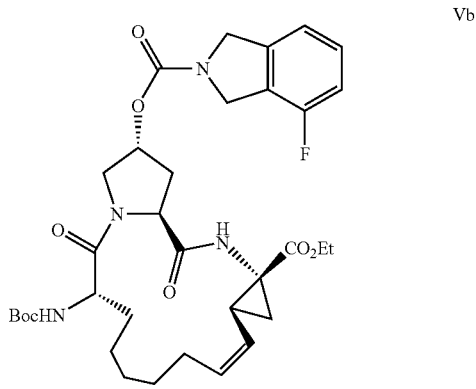

Vb

The hydrolysis can usually be accomplished by treatment of the ester with an aqueous alkali hydroxide solution such as with an aqueous sodium hydroxide solution in solvents like methanol or ethanol at a temperature of 0° C. to 40° C.

After neutralization of the reaction mixture, usually with hydrochloric acid, the macrocyclic acid of formula VI can be isolated extraction with a suitable solvent such as with dichloromethane. Crystallization in a suitable solvent, preferably in tetrahydrofuran, leads to a crystalline product with a purity of over 98%.

Step (c)

Step c is the coupling of the macrocyclic acid of formula VI with cyclopropyl sulfonamide to form the macrocyclic sulfonamide of formula VII.

In a one embodiment the macrocyclic acid of formula VIb is used.

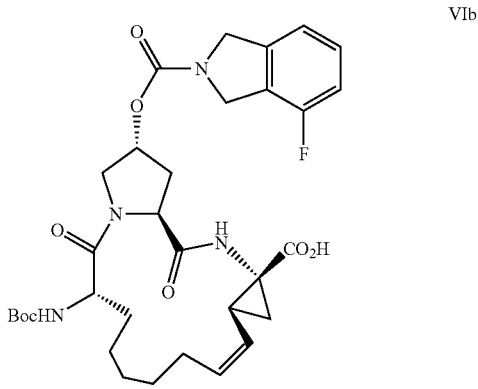

VIb

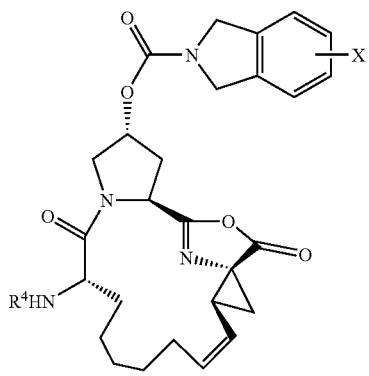

IX

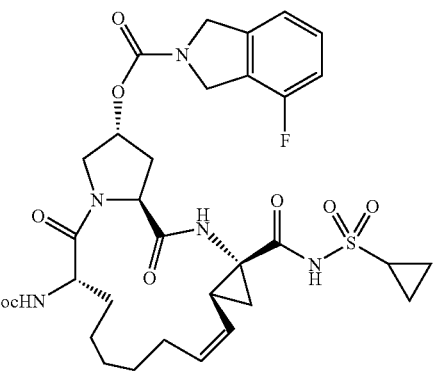

VIIb

The macrocyclic acid of formula VI is reacted with acetic acid anhydride in the presence of an inorganic base, such as with an alkali carbonate like sodium carbonate and a suitable organic solvent such as with tetrahydrofuran to afford an azlactone intermediate of the formula IX wherein $R^4$ is an amino protecting group and X is halogen. The reaction is expediently performed at a temperature of 10° C. to 50° C.

As a rule the azlacton intermediate is formed in situ but not be isolated and immediately further reacted with cyclopropyl sulfonamide in the presence of an inorganic base, such as with an alkali carbonate like potassium carbonate to the macrocyclic sulfonamide of formula VII.

The reaction in this second step is expediently performed at a temperature of 50° C. to 70° C.

Upon completion of the reaction the reaction mixture can be treated with water. After separation and removal of the water phase the organic phase may further be diluted with a suitable organic solvent such as with ethyl acetate or toluene and washed e.g. with an aqueous sulphuric acid and water.

Isolation of the macrocyclic sulfonamide of formula VII can then be accomplished by a solvent switch to ethanol followed by addition of the ethanolic solution to water thereby causing precipitation of the desired product.

In a one embodiment the macrocyclic sulfonamide of formula VII is not isolated, but the organic phase which has been treated as herein before described will be dried by continuous azeotropic distillation.

The mixture can then directly be used for subsequent step (d).

Step (d)

Step d is a salt formation by treating the macrocyclic sulfonamide VII with a sodium base to form the macrocyclic compound of formula III. In one embodiment the macrocyclic sulfonamide of the formula VIIb is used.

As a rule the anhydrous solution obtained from step (c) is treated with a sodium base sodium hydroxide, preferably an aqueous solution thereof, sodium methylate or sodium ethoxide, preferably with sodium methylate in the presence of methanol at a temperature of 0° C. and 50° C.

Upon completion of the reaction the reaction mixture can be treated with a mixture of a suitable organic solvent such as ethyl acetate and water where after the crystals of the sodium compound of formula III, preferably the compound of formula VIII can be collected in good purity and yield.

The following examples illustrate the preparation of compounds and processes within the scope of the invention. These examples and preparations that follow are provided to enable those skilled in the art to more clearly understand and to practice the present invention. They should not be considered as limiting the scope of the invention, but merely as being illustrative and representative thereof.

EXAMPLES

Abbreviations:

r.t.=room temperature

Boc=tert-butoxycarbonyl $ImH_2Mes$=1,3-bis-(2,4,6-tiimethylphenyl)-2-imidazolidinylidene ImMes=1,3-bis-(2,4,6-trimethylphenyl)-2-imidazolylidene $ImH_2Pr$=1,3-bis-(2,6-diisopropylphenyl)-2-imidazolidinylidene RCM=ring closing metathesis RP column=reverse phase column S/C=molar substrate-to-catalyst ratio Mes=2,4,6-trimethylphenyl Cy=cyclohexyl Cyp=cyclopentyl Diene IVb=4-Fluoro-1,3-dihydro-isoindole-2-carboxylic acid (3R,5S)-1-((S)-2-tert-butoxycarbonylamino-non-8-enoyl)-5-((1R,2S)-1-ethoxycarbonyl-2-vinyl-cyclopropyl-carbamoyl)-pyrrolidin-3-yl ester of the formula

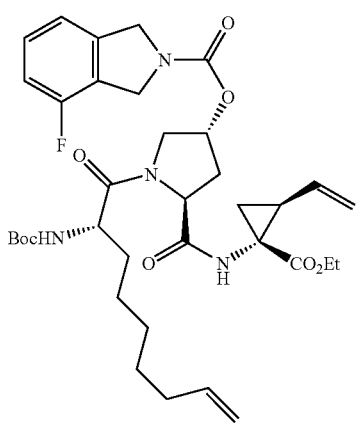

RCM-Ester Vb=(2R,6S,12Z,13aS,14aR,16aS)-Cyclopropa[e]pyrrolo[1,2-a][1,4]diazacyclopentadecine-14a(5H)-carboxylic acid, 6-[[(tert-butoxy)carbonyl]amino]-2-[[(4-fluoro-1,3-dihydro-2H-isoindol-2-yl)carbonyl]oxy]-1,2,3,6,7,8,9,10,11,13a,14,15,16,16a-hexadecahydro-5,16-dioxo-, ethyl ester The atom numbering is as shown below:

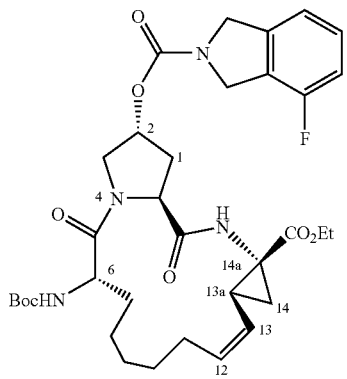

Epi-Vb=13aR epimer of RCM ester of formula Vb

Epi-IVb: epimer at the vinyl substituted carbon atom of cyclopropyl unit in IVb a %=HPLC area %

TABLE II

| Catalyst Nr. | Catalyst Structure | Chemical Short Name |
|---|---|---|
| A | (structure shown) | [RuCl$_2$(=CHPh)(ImH$_2$Mes)(m-Br-Pyr)$_2$]<br>CAS No. 477218-66-9; a) |
| B | (structure shown) | [RuCl$_2$(=CH(o-OCH(Me)CO$_2$Me)-Ph)(ImH$_2$Mes)]<br>CAS No. 837392-94-6 |
| C | (structure shown) | [RuCl$_2$(=CH(o-OCH(Me)CO$_2$H)-Ph)(ImH$_2$Mes)]<br>CAS No. 959710-27-1 |

TABLE II-continued
| Catalyst Nr. | Catalyst Structure | Chemical Short Name |
|---|---|---|
| D | 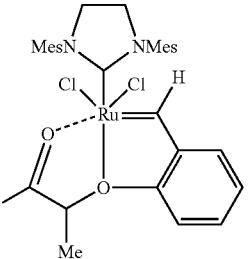 | [RuCl$_2$(=CH(o-OCH(Me)CONEt$_2$)Ph)-(ImH$_2$Mes)] |
| E | 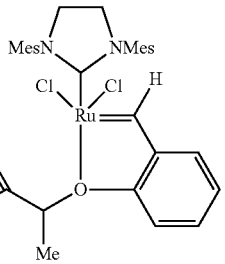 | [RuCl$_2$(=CH(o-OCH(Me)CONH$_2$)-Ph)(ImH$_2$Mes)] |
| F | 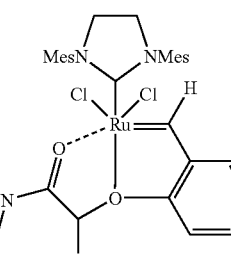 | [RuCl$_2$(=CH(o-OCH(Me)CO-N-Morpholine)Ph)(ImH$_2$Mes)] |
| G | 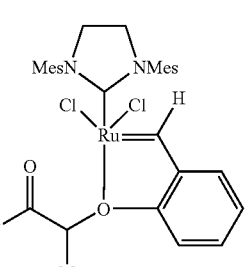 | [RuCl$_2$(=CH(o-OCH(Me)CONHPh)Ph)(ImH$_2$Mes)] |
| H | 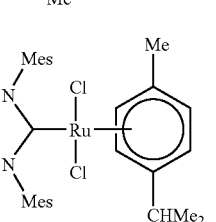 | [RuCl$_2$(ImMes)(p-cymene)]<br>CAS NO 244187-82-4 |
| J | 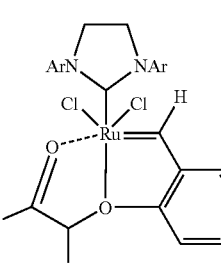 | [RuCl$_2$(=CH(o-OCH(Me)CO-N-Pyrrolidine)Ph)(ImH$_2$Mes)] |

TABLE II-continued

| Catalyst Nr. | Catalyst Structure | Chemical Short Name |
|---|---|---|
| K | | [RuCl$_2$(=CH(o-OCH(Me)CO-N-Pyrrolidine)Ph)(PCy$_3$)] |
| L | Naph = 2,7-di-isopropyl-naphth-1-y | [RuCl$_2$(=CH(o-OCH(Me)CO-N-Pyrrolidine)Ph)(SIPrNap)] |
| M | | [RuCl$_2$(=CH(o-OCMe$_2$CO-N-Pyrrolidine)Ph)(ImH$_2$Mes)] |
| N | | [RuCl$_2$(=CH(o-OCH$_2$CO-N-Pyrrolidine)Ph)(ImH$_2$Mes)] | a) Commercially available from Sigma-Aldrich Chemie GmbH, Postfach, CH-9471 Buchs, Switzerland.

Example 1

In a glove-box (O$_2$ concentration <2 ppm) a solution of 50.0 mg (0.073 mmol, corrected by content) of diene IVb and 2.62 mg (0.0036 mmol) of catalyst D in 6.5 mL of toluene (distilled under argon) was stirred at 65° C. in a 15 mL screw-capped flask. After 4 h one drop of ethylene diamine was added and the mixture was stirred for 10 min outside of the glove box. To this solution was added 1 mL of 1 M aqueous solution of hydrochloric acid the biphasic mixture was stirred for 10 min. A 0.5 mL aliquot of the organic phase was removed and evaporated to dryness; the oily residue was dissolved in 1 mL of acetonitrile and analyzed by HPLC. Conversion was >99 area %, the desired product (RCM-ester Vb) had a 67 area % purity.

HPLC method on a reverse phase (RP) column: Waters XBridge C18 column, 4.6×150 mm, solvent A: water/acetonitrile 95/5, solvent B: acetonitrile, gradient from A/B 50/50 to 10/90 over 11 min, then 4 min at 10/90, 40° C., UV detector 210 nm, 1 mL/min flow rate. Retention times: toluene 5.2 min, diene IVb 8.85 min, RCM-ester Ib 6.97 min (identified by HPLC/MS, [MH]$^+$ 657.4 u), peaks of dimeric by-products at 10.2, 10.4, 12.1 and 13.1 min (MS: [MH]$^+$ 1313 u). Only the sum of the dimer peaks is given in the tables and experiments.

HPLC method on chiral column: Chiralcel OD-RH, 4.6-150 mm, solvent A: water+5% acetonitrile (62%), acetonitrile (38%), no gradient, 40° C., flow rate 1 mL/min, Lw detector 210 nm. Retention times: diene IVb 3.4 min, 2R epimeric diene epi-IVb74.2 min, RCM ester Vb 47.6 min, at 13a epimeric RCM-ester V (EpiVb) 33.9 min.

Examples 2a-2h

The examples in Table 1 were carried out using the same procedure and conditions (if not specifically mentioned in the footnote) as in Example 1 but in the presence of various catalysts.

TABLE 1

| Reaction Nr. | Catalyst Nr. | RP column | | | chiral column | |
|---|---|---|---|---|---|---|
| | | Diene IVb (a %) | RCM-ester Vb (a %) | Dimers (a %) | RCM ester Vb (a %) | Vb/epi-Vb |
| 2a | A | 6 | 74 | 11 | 74 | 99/1 |
| 2b | C | 0.2 | 78 | 16 | 82 | 99/1 |
| 2c | B | 2 | 58 | 13 | 62 | 77/23 |
| 2d | E | 1 | 72 | 18 | 79 | 99/1 |
| 2e | F | 0.3 | 67 | 14 | 88 | 89/11 |
| 2f | G | 0.3 | 77 | 16 | 99 | >99/1 |
| 2g | H | 31 | 37 | 3 | 48 | 84/16 |
| 2h | J | 0.2 | 64 | 13 | 85 | 86/14 |

% y. = % yield determined by HPLC with internal standard;
a %: HPLC area %;
n.d.: not determined.
Reaction Nr. 2 g was run at 80° C. under addition of 0.007 mmol of phenylacetylene.

Example 3

S/C 135-200

To a solution of 2.67 g (2.00 mmol) of diene IVb (as a 51.4% solution in toluene) in 155 mL of toluene was added under argon bubbling (33 mL/min) at 60° C. 6.58 mg (0.005 mmol) of catalyst E. After 2 h stirring at this temperature (an analytical sample was taken, if required) 3.26 mg of catalyst E were added. After a total of 5 h 50 µl (0.74 mmol) of ethylenediamine were added and the mixture was stirred at room temperature for 10 min. After this time the mixture was extracted with 1 M aqueous solution of hydrochloric acid and with water. Evaporation of the organic phase afforded 1.32 g of RCM-ester Vb with 78.5% purity.

Examples 4a-4f

S/C 135-200

The examples in Table 2 were carried out using the same procedure and conditions as in Example 3, but in the presence of various catalysts.

TABLE 2

| Reaction Nr. | Catalyst Nr. | RP column | | | chiral column | |
|---|---|---|---|---|---|---|
| | | Diene IV b a % | RCM-Ester Vb a % | Dimers a % | RCM-Ester Vb a % | Epi-Vb a % |
| 4a | D | 23 | 59 | 5 | >99.8 | <0.2 |
| 4b | B | 5 | 76 | 12 | >99.8 | <0.2 |
| 4c | C | 0.5 | 80 | 14.6 | >99.8 | <0.2 |
| 4d | F | 28 | 55 | 4 | 68 | <0.2 |
| 4e | G | 2.7 | 78 | 13 | >99.8 | <0.2 |
| 4f | J | 18 | 64 | 6 | >99.8 | <0.2 |

% y. = % yield determined by HPLC with internal standard;
a %: HPLC area %;

Example 5

S/C 1000, vacuum, P=0.26 bar

To a solution of 6.60 g (5.00 mmol) of diene IVb (as a 51.4% solution in toluene) in 390 mL of toluene was added at 70° C. under vacuum (pressure=ca. 0.26 bar) by dropping funnel a solution of 3.59 mg (0.005 mmol) of catalyst D in 20 mL of toluene. The catalyst was added during ca. 1 h. Under these conditions a small amount of toluene (19 mL) distilled off in the course of the reaction. After 2 h of total reaction time 17 µl (0.252 mmol) of ethylene diamine were added at ambient pressure, the reaction mixture was concentrated under vacuum, washed with 0.5 M aqueous solution of hydrochloric acid, treated with decolorizing charcoal and evaporated to dryness. RCM-ester Vb was isolated as a off-white solid (3.58 g) with 84.2 a % purity (75.7% content, 82.5% yield).

Examples 6a-f

The experiments in Table 3 have been carried out in analogy to Example 5, Catalyst Nr., temperature, reaction time, yield and purity of RCM ester Vb are given in the table.

TABLE 3

| Reaction Nr. | Catalyst Nr. | T °C. | RP column | | | chiral column | |
|---|---|---|---|---|---|---|---|
| | | | Diene IVb a % | RCM-Ester Vb a %/% y. | Dimers a % | RCM-Ester Vb a % | Epi-Vb a % |
| 6a | B | 70 | 0.2 | 84/83 | 12.2 | >99.8 | <0.2 |
| 6b | C | 70 | 1.6 | 84/81 | 10.0 | 99.8 | 0.2 |
| 6c | E | 70 | 1.4 | 83/82 | 10.3 | >99.8 | <0.2 |
| 6d | F | 70 | 0.3 | 83/85 | 13.4 | >99.8 | <0.2 |
| 6e$ | G | 70 | 1.7 | 83/82 | 10 | >99.8 | <0.2 |
| 6f | J | 70 | 0.3 | 84/— | 11 | >99.8 | <0.2 |

% y. = % yield determined by HPLC with internal standard;
a %: HPLC area %
$Total reaction time was 4 h.

Examples 7a-e

The experiments in Table 4 have been carried out in analogy to example 5, but with following changes: 10 mmol of diene IVb in 780 mL of toluene, catalyst (type and amount cf. Table 4) added during ca. 1.5 h as a solution in 40 mL of toluene, temperature 70° C.

TABLE 4

| Reaction Nr. | Catalyst Nr. | S/C | RP column | | | chiral column | |
|---|---|---|---|---|---|---|---|
| | | | Diene IVb a % | RCM-Ester Vb a %/% y. | Dimers a % | RCM-Ester Vb a % | Epi-Vb a % |
| 7a | D | 2000 | 1.7 | 83/83 | 10 | >99.8 | <0.2 |
| 7b$ | D | 2500 | 4.3 | 82/79 | 9 | >99.8 | <0.2 |
| 7c# | E | 2000 | 2.5 | 83/80 | 9 | >99.8 | <0.2 |
| 7d£ | E | 2200 | 4.5 | 79/— | 10 | >99.8 | <0.2 |
| 7e | F | 2200 | 1.2 | 84/83 | 1.2 | >99.8 | <0.2 |

% y. = % yield determined by HPLC with internal standard;
a %: HPLC area %
$Total reaction time was 2.5 h, the catalyst was added during 1.5 h.
Total reaction time was 4 h.
£Total reaction time was 5 h.

Example 8

2-[((E,Z)-2-propenyl)-phenoxy]-propionamide

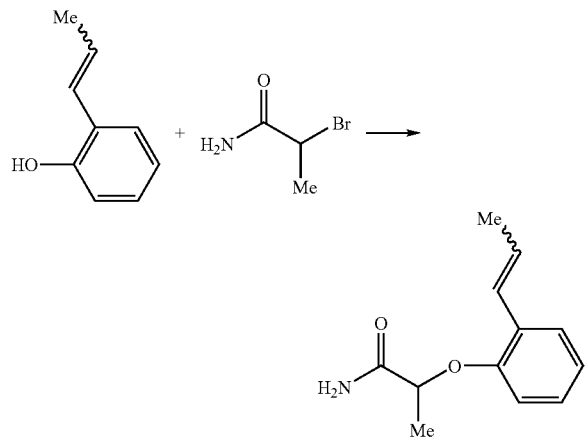

To a suspension of 12.24 g (87.6 mmol) of potassium carbonate and 5.78 g (17.7 mmol) of cesium carbonate in 200 mL of N,N-dimethylformamide, 6.00 g (43.8 mmol) of (E,Z)-2-propenylphenol (4:1 mixture of E/Z-isomers) was added. After stirring for 30 min at room temperature, 6.73 g (43.8 mmol) of 2-bromo-propionamide was added and the reaction mixture was stirred for 2 days at 40° C. The reaction mixture was filtered and concentrated at 50° C./10 bar). To the residue, 150 mL of diethyl ether and 150 mL of water were added. The layers were separated and the aqueous layer extracted with 200 mL of diethyl ether. The combined organic layers were washed successively with 100 mL of water and 100 mL of brine, dried over sodium sulfate and evaporated to dryness at 40° C./10 mbar to yield 9.44 g (96%) of the title compound as a 3.5:1 mixture of E/Z-isomers with 91% purity (GC-area %) as white crystals. (GC method: Column HP-5, 5% phenyl methyl siloxane, 30 m×0.32 mm, df: 0.25 µm; injector temp.: 250° C.; detector temp.: 250° C.; oven temp.: 50° C. to 300° (10° C./min), then 300° C. for 5 min; retention times: 2-bromo-propionamide 4.8 min, (Z)-2-propenylphenol 6.7 min, (E)-2-propenylphenol 8.5 min, 2-[((Z)-2-propenyl)-phenoxy]-propionamide at 14.3 min, 2-[((E)-2-propenyl)-phenoxy]-propionamide 15.0 min). MS: 206.0 (M+H⁺).

Example 9

2-[((E,Z)-2-Propenyl)-phenoxy]-propionic acid

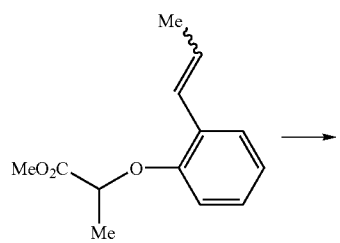

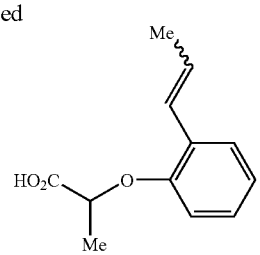

To a solution of 0.50 g (2.2 mmol) of methyl 2-[((E,Z)-2-propenyl)-phenoxy]-propanoate (4:1 mixture of E/Z-isomers, prepared according to D. Arlt, K. Grela et al, *J. Am. Chem. Soc.* 2006, 128, 13652-13653) in dioxane, 11 mL (20.0 mmol) of a 2M aqueous sodium hydroxide solution was added and the reaction mixture was stirred for 16 h at room temperature. To the reaction mixture, 50 mL of water and 100 mL of tert.-butyl methyl ether were added. The organic layer was washed with 40 mL of water. After the pH of the combined aqueous layers was adjusted with 25% aqueous hydrochloric acid to a value of 1, 150 mL of dichloromethane was added. The organic layer was washed with 100 mL of brine, dried over sodium and evaporated to dryness at 40° C./10 mbar to yield 0.50 g (99% yield) of the title compound as a 3:1 mixture of E/Z-isomers with >99.9% purity (GC-area %) as white crystals. (GC method as described in Example 7. Retention times: Methyl 2-[((Z)-2-propenyl)-phenoxy]-propanoate 12.2 min, methyl 2-[((E)-2-propenyl)-phenoxy]-propanoate 12.9 min, 2-[((Z)-2-propenyl)-phenoxy]-propionic acid 13.3 min, 2-[((E)-2-propenyl)-phenoxy]-propionic acid 14.0 min). Mp.: 96° C. MS: 206.0 (M⁺).

Example 10

N,N-Diethyl-2-[((E. Z)-2-propenyl)-phenoxy]-propionamide

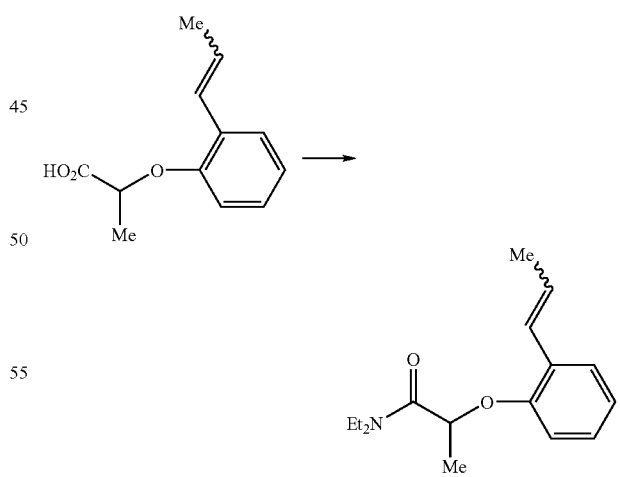

To a solution 1.26 mL (12.1 mmol) of diethylamine in 100 mL of N,N-dimethylformamide, 2.12 mL (12.1 mmol) of N,N-diisopropylethylamine, 0.50 g (2.4 mmol) of 2-[((E,Z)-2-propenyl)-phenoxy]-propionic acid (3:1 mixture of E/Z-isomers) and 1.01 g (3.0 mmol) of O-benzotriazol-1-yl-N,N',N'-tetramethyluronium tetrafluoroborate (TBTU) was added and the reaction mixture stirred for 16 h at room temperature.

To the reaction mixture 100 mL of water and 200 mL ethyl acetate were added. The organic layer was separated, washed with 50 mL of water, dried over sodium sulfate and evaporated to dryness at 40° C./10 mbar. The crude title product was purified by silica gel chromatography (heptane/ethyl acetate 3:1) to yield 0.57 g (87% yield) of the title compound as a 4:1 mixture of E/Z-isomers with 96.2% purity (GC-area %) as a colorless oil. (GC method as described in Example 7. Retention times: 2-[((Z)-2-propenyl)-phenoxy]-propanoic acid 13.9 min, 2-[((E)-2-propenyl)-phenoxy]-propanoic acid 14.0 min. N,N-diethyl-2-[((Z)-2-propenyl)-phenoxy]-propionamide 16.2 min, N,N-diethyl-2-[((E)-2-propenyl)-phenoxy]-propionamide 16.6 min). MS: 262.0 (M+H⁺).

Example 11

1-Morpholine-4-yl-2-[((E. Z)-2-propenyl)-phenoxy]-propan-1-one

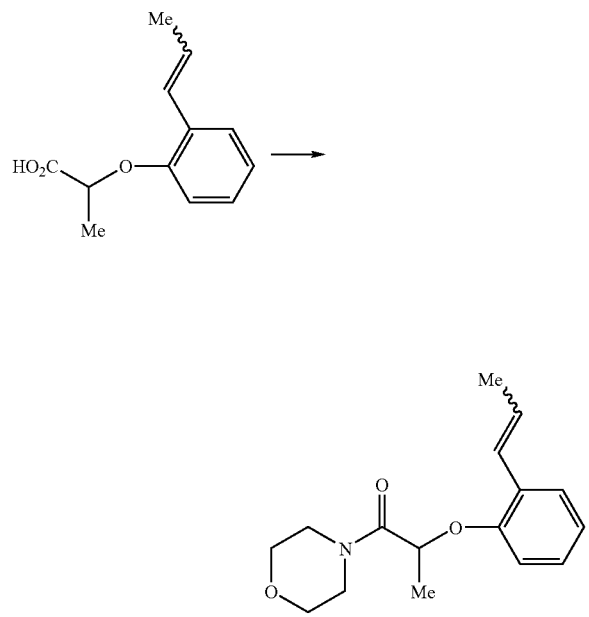

To a solution 0.21 mL (2.4 mmol) of morpholine in 13 mL of N,N-dimethylformamide, 0.42 mL (2.4 mmol) of N,N-diisopropylethylamine, 0.10 g (0.5 mmol) of 2-[((E,Z)-2-propenyl)-phenoxy]-propionic acid (3:1 mixture of E/Z-isomers) and 0.20 g (0.6 mmol) of O-benzotriazol-1-yl-N,N,N',N'-tetramethyluronium tetrafluoroborate (TBTU) was added and the reaction mixture stirred for 45 min at room temperature. To the reaction mixture 20 mL of water and 40 mL ethyl acetate were added. The organic layer was separated, washed with 10 mL of water, dried over sodium sulfate and evaporated to dryness at 40° C./10 mbar. The crude title product was purified by silica gel chromatography (heptane/ethyl acetate 3:1) to yield 71 mg (53% yield) of the title compound as a 4:1 mixture of E/Z-isomers with >99.9% purity (GC-area %) as a white powder. (GC method as described in Example 7. Retention times: 2-[((Z)-2-propenyl)-phenoxy]-propanoic acid 13.9 min, 2-[((E)-2-propenyl)-phenoxy]-propanoic acid 14.0 min, 1-morpholine-4-yl-2-[((Z)-2-propenyl)-phenoxy]-propan-1-one 18.4 min, 1-morpholine-4-yl-2-[((E)-2-propenyl)-phenoxy]-propan-1-one 18.7 min). MS: 276.1 (M+H⁺).

Example 12

N-Phenyl-2-[((E. Z)-2-propenyl)-phenoxy]-propionamide

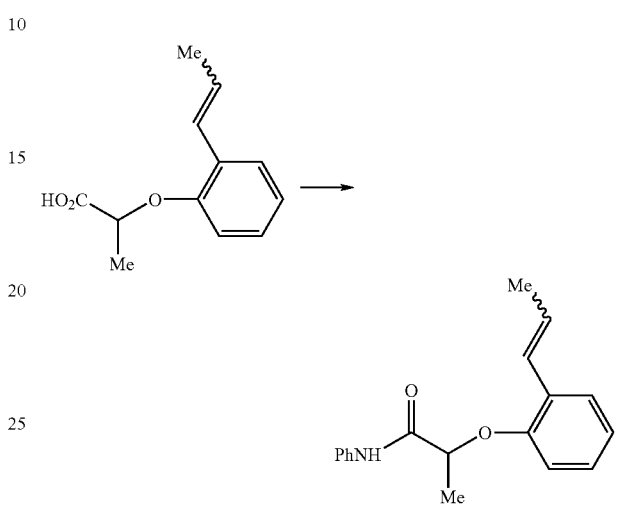

To a solution 0.11 mL (1.2 mmol) of aniline in 6 mL of N,N-dimethylformamide, 0.21 mL (1.2 mmol) of N,N-diisopropylethylamine, 0.05 g (0.3 mmol) of 2-[((E,Z)-2-propenyl)-phenoxy]-propionic acid (3:1 mixture of E/Z-isomers) and 0.10 g (0.3 mmol) of O-benzotriazol-1-yl-N,N,N',N'-tetramethyluronium tetrafluoroborate (TBTU) was added and the reaction mixture stirred for 2 h at room temperature. To the reaction mixture 10 mL of water and 20 mL ethyl acetate were added. The organic layer was separated, washed with 10 mL of water, dried over sodium sulfate and evaporated to dryness at 40° C./10 mbar. The crude title product was purified by silica gel chromatography (heptane/ethyl acetate 3:1) to yield 58 mg (85% yield) of the title compound as a 4:1 mixture of E/Z-isomers with >99.9% purity (GC-area %) as a white powder. (GC method as described in Example 7. Retention times: 2-[((Z)-2-propenyl)-phenoxy]-propanoic acid 13.9 min, 2-[((E)-2-propenyl)-phenoxy]-propanoic acid 14.0 min, N-phenyl-2-[((Z)-2-propenyl)-phenoxy]-propionamide 19.9 min, N-phenyl-2-[((E)-2-propenyl)-phenoxy]-propionamide 20.3 min). MS: 282.3 (M+H⁺).

Example 13

2-[((E,Z)-2-Propenyl)-phenoxy]-1-pyrrolidine-1-yl-propan-1-one

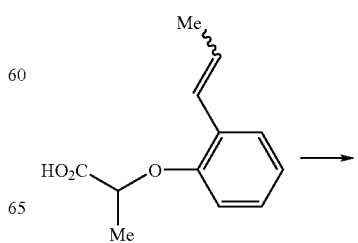

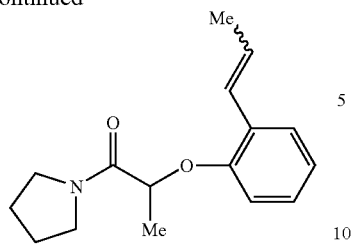

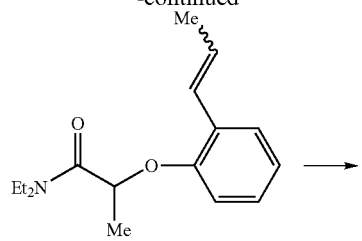

To a solution 1.92 mL (23.0 mmol) of pyrrolidine in 200 mL of N,N-dimethylformamide, 4.02 mL (23.0 mmol) of N,N-diisopropylethylamine, 1.00 g (4.6 mmol) of 2-[((E,Z)-2-propenyl)-phenoxy]-propionic acid (3:1 mixture of E/Z-isomers) and 1.92 g (5.8 mmol) of O-benzotriazol-1-yl-N,N,N',N'-tetramethyluronium tetrafluoroborate (TBTU) was added and the reaction mixture stirred for 2 h at room temperature. To the reaction mixture 200 mL of water and 400 mL ethyl acetate were added. The organic layer was separated, washed with 100 mL of water, dried over sodium sulfate and evaporated to dryness at 40° C./10 mbar. The crude title product was purified by silica gel chromatography (heptane/ethyl acetate 3:1) to yield 0.69 g (57% yield) of the title compound as a 4:1 mixture of E/Z-isomers with 98.1% purity (GC-area %) as a white powder. (GC method as described in Example 7. Retention times: 2-[((Z)-2-propenyl)-phenoxy]-propanoic acid 13.9 min, 2-[((E)-2-propenyl)-phenoxy]-propanoic acid 14.0 min, 2-[((Z)-2-propenyl)-phenoxy]-1-pyrrolidine-1-yl-propan-1-one $\overline{18.0}$ min, 2-[((E)-2-propenyl)-phenoxy]-1-pyrrolidine-1-yl-propan-1-one $\overline{18.4}$ min). MS: 260.0 (M+H$^+$).

Example 14

Catalyst No. D, [RuCl$_2$(=CH(o-OCH(Me)CONEt$_2$)Ph)(ImH$_2$Mes)]

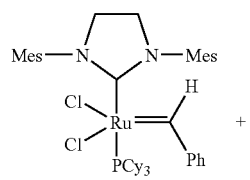

A suspension of 1.50 g (1.77 mmol) of [RuCl$_2$(PCy$_3$)(ImH$_2$Mes)(phenylmethylene)] (commercially available from Sigma-Aldrich Inc., St. Louis, USA), 0.19 g (1.94 mmol) of copper chloride and 0.51 g (1.94 mmol) of N,N-diethyl-2-[((E,Z)-2-propenyl)-phenoxy]-propionamide as a 4:1 mixture of E/Z-isomers in 110 mL of dichloromethane was stirred for 40 min at 40° C. The reaction mixture was evaporated to dryness at 40° C./10 mbar. The crude title product was purified by repeated digestion with ethyl acetate/pentane/tetrahydrofuran to yield 0.73 g (58%) of the title compound as a green crystalline solid. MS: 711.2 (M$^+$). Anal. calcd. for C$_{35}$H$_{45}$Cl$_2$N$_3$O$_2$Ru: C, 59.06; H, 6.37; N, 5.90; Cl, 9.96. Found: C, 58.56; H, 6.44; N, 5.23; Cl, 9.86.

Crystals of the title compound suitable for X-ray crystal structure analysis were grown by vapor diffusion of pentane into a solution of 20 mg of [RuCl$_2$(=CH(o-OCH(Me)CONEt$_2$)Ph)(ImH$_2$Mes)] in 2 mL of tetrahydrofuran at room temperature. FIG. 1 shows a labeled view of the complex of formula D.

TABLE X1

| Crystal data and structure refinement for complex D | |
|---|---|
| Empirical formula | C$_{35}$H$_{45}$Cl$_2$N$_3$O$_2$Ru |
| Formula weight | 711.71 |
| Crystal habit | Green, cubical |
| Temperature | 110 K |
| Wavelength | 0.7107 Å |
| Crystal system, space group | Monoclinic, C2/c |
| Unit cell dimensions | a = 30.5023(11) Å; alpha = 90 deg. |
|  | b = 13.0991(4) Å; beta = 102.893(4) deg. |
|  | c = 17.1676(5) Å; gamma = 90 deg. |
| Volume | 6686.4(4) Å$^3$ |
| Z, Calculated density | 8, 1.414 Mg/m$^3$ |
| Absorption coefficient | 0.664 mm$^{-1}$ |
| F(000) | 2960 |
| Crystal size | 0.18 × 0.18 × 0.15 mm |
| Theta range for data collection | 3.04 to 26.37 deg. |
| Limiting indices | $-38 \leq h \leq 38, -15 \leq k \leq 16, -21 \leq 1 \leq 21$ |

TABLE X1-continued

Crystal data and structure refinement for complex D

| | |
|---|---|
| Reflections collected/unique | 24158/6073 [R(int) = 0.0362] |
| Completeness to theta = 26.37 | 88.7% |
| Absorption correction | Semi-empirical from equivalents |
| Max. and min. transmission | 1.00000 and 0.84916 |
| Refinement method | Full-matrix least-squares on $F^2$ |
| Data/restraints/parameters | 6073/0/401 |
| Goodness-of-fit on $F^2$ | 0.966 |
| Final R indices [I > 2sigma(I)] | R1 = 0.0291, wR2 = 0.0727 |
| R indices (all data) | R1 = 0.0426, wR2 = 0.0764 |
| Largest diff. peak and hole | 0.415 and −0.476 e.A$^{-3}$ |

TABLE X2

Selected Bond Lengths (Å) and Angles (deg) for Complex D

| Bond Lengths (Å) | |
|---|---|
| Ru(1) C(15) | 1.840(2) |
| Ru(1) C(23) | 1.984(2) |
| Ru(1) O(4) | 2.1873(16) |
| Ru(1) O(5) | 2.3494(16) |
| Ru(1) Cl(2) | 2.3692(6) |
| Ru(1) Cl(3) | 2.4023(6) |
| Bond Angles (deg) | |
| C(15)-Ru(1)-C(23) | 99.12(10) |
| C(15)-Ru(1)-O(4) | 80.90(8) |
| C(23)-Ru(1)-O(4) | 173.37(8) |
| C(15)-Ru(1)-O(5) | 147.19(9) |
| C(23)-Ru(1)-O(5) | 112.54(8) |
| O(4)-Ru(1)-O(5) | 68.66(6) |
| C(15)-Ru(1)-Cl(2) | 100.04(8) |
| C(23)-Ru(1)-Cl(2) | 89.05(7) |
| O(4)-Ru(1)-Cl(2) | 84.43(5) |
| O(5)-Ru(1)-Cl(2) | 89.22(4) |
| Cl(2)-Ru(1)-Cl(3) | 170.68(2) |

Example 15

Catalyst No. D, [RuCl$_2$(=CH(o-OCH(Me)CONEt$_2$)Ph)(ImH$_2$Mes)]

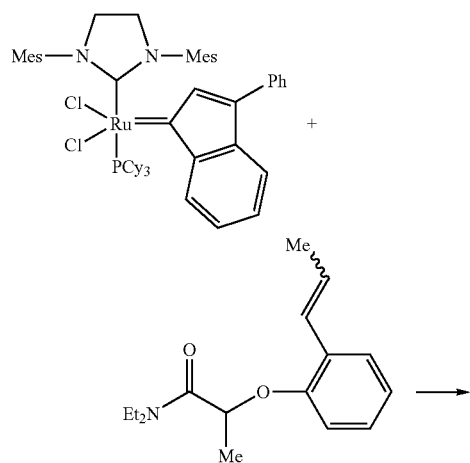

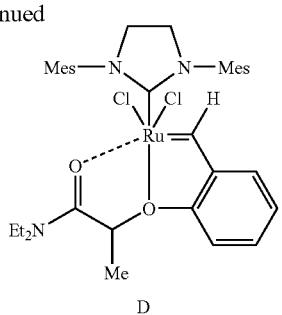

D

A suspension of 0.50 g (0.53 mmol) of [RuCl$_2$(PCy$_3$)(ImH$_2$Mes)(3-phenyl-indenylidene)] (commercially available from Umicore AG, D-63457 Hanau-Wolfgang), 0.06 g (0.59 mmol) of copper chloride and 0.16 g (0.53 mmol) of N,N-diethyl-2-[((E,Z)-2-propenyl)-phenoxy]-propionamide as a 4:1 mixture of E/Z-isomers in 16 mL of dichloromethane was stirred for 40 min at 40° C. The reaction mixture was evaporated to dryness at 40° C./10 mbar. The residue was stirred in 45 mL of tetrahydrofuran for 15 mm at room temperature. The dark green suspension was filtered and the filtrate was evaporated to dryness at 40° C./10 mbar. The crude title product was purified by repeated digestion with ethyl acetate/pentane to yield 0.29 g (76%) of the title compound as a green crystalline solid. MS: 711.2 (M$^+$).

Example 16

Catalyst No. F, [RuCl$_2$(=CH(o-OCH(Me)CO—N-Morpholine)Ph)(ImH$_2$Mes)]

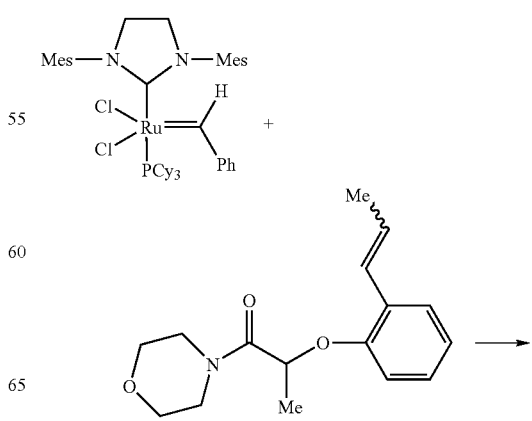

-continued

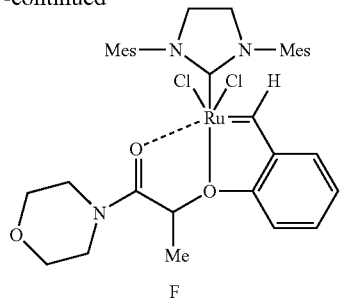

F

A suspension of 1.00 g (1.18 mmol) of [RuCl$_2$(PCy$_3$) (ImnH$_2$Mes)(phenylmethylene)] (commercially available from Sigma-Aldrich Inc., St. Louis, USA), 0.13 g (1.30 mmol) of copper chloride and 0.36 g (1.30 mmol) of 1-morpholine-4-yl-2-[((E,Z)-2-propenyl)-phenoxy]-propan-1-one as a 4:1 mixture of E/Z-isomers in 75 mL of dichloromethane was stirred for 30 min at 40° C. The reaction mixture was evaporated to dryness at 40° C./10 mbar. The residue was stirred in 250 mL of ethyl acetate for 30 min at room temperature. The dark green suspension was filtered and the filtrate was evaporated to dryness at 40° C./10 mbar. The crude title product was purified by silica gel chromatography (cyclohexane/ethyl acetate 1:2) to yield 0.38 g (45% yield) of the title compound as a green powder. MS: 725.2 (M$^+$). Anal. calcd. for C$_{35}$H$_{43}$Cl$_2$N$_3$O$_3$Ru.½CH$_2$Cl$_2$: C, 55.51; H, 5.77; N, 5.47; Cl, 13.85. Found: C, 54.75; H, 5.76; N, 5.30; Cl, 13.71.

Figure 2:
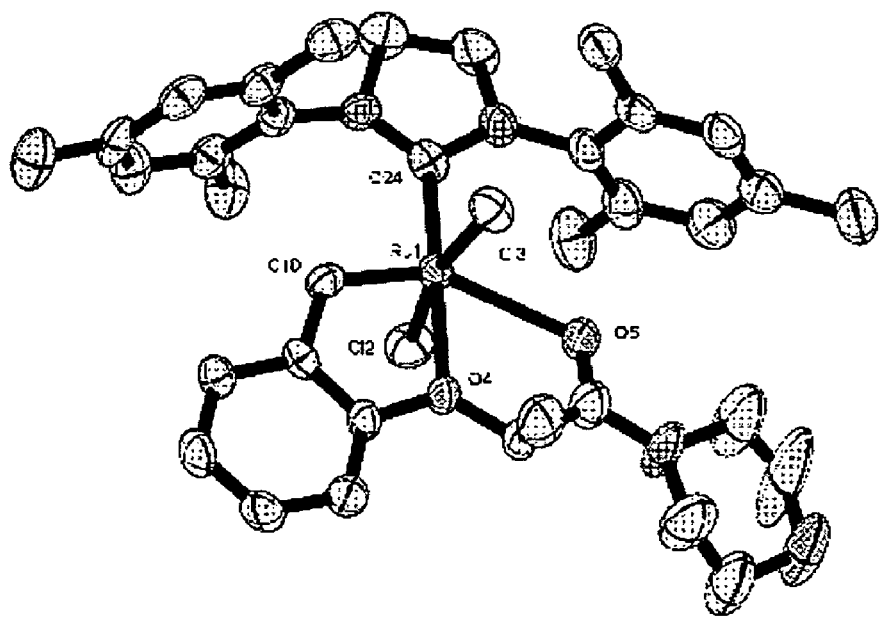
FIG. 2 is an Ortep plot of RuCl$_2$(=CH(o-OCH(Me)CO—N-morpholine)Ph)(ImH$_2$Mes) (formula F). The collection and the refinement of parameters for the crystallographic analysis are summarized in Table X3 and representative bond lengths and bond angles are reported in Table X4 in the examples section.

Crystals of the title compound suitable for X-ray crystal structure analysis were grown by vapor diffusion of pentane into a solution of 10 mg of [RuCl$_2$(=CH(o-OCH(Me)CO—N-Morpholine)Ph)(ImrH$_2$Mes)] in 0.5 mL of dichloromethane at room temperature. FIG. 2 shows a labeled view of the complex of formula F.

TABLE X4

Selected Bond Lengths (Å) and Angles (deg) for Complex F

Bond Lengths (Å)

| | |
|---|---|
| Ru(1) C(10) | 1.833(6) |
| Ru(1) C(24) | 2.000(6) |
| Ru(1) O(4) | 2.221(4) |
| Ru(1) O(5) | 2.4966(43) |
| Ru(1) Cl(3) | 2.3566(15) |
| Ru(1) Cl(2) | 2.3787(16) |

Bond Angles (deg)

| | |
|---|---|
| C(10)-Ru(1)-C(24) | 100.5(2) |
| C(10)-Ru(1)-O(4) | 79.6(2) |
| C(24)-Ru(1)-O(4) | 178.9(2) |
| C(10)-Ru(1)-O(5) | 145.73(20) |
| C(24)-Ru(1)-O(5) | 113.76(19) |
| O(4)-Ru(1)-O(5) | 66.08(14) |
| C(10)-Ru(1)-Cl(2) | 94.76(18) |
| C(24)-Ru(1)-Cl(2) | 90.84(16) |
| O(4)-Ru(1)-Cl(2) | 88.04(11) |
| O(4)-Ru(1)-Cl(3) | 87.93(11) |
| Cl(2)-Ru(1)-Cl(3) | 167.82(6) |

TABLE X3

Crystal data and structure refinement for complex F

| | |
|---|---|
| Empirical formula | C$_{35}$H$_{45}$Cl$_2$N$_3$O$_2$Ru |
| Formula weight | 777.67 |
| Crystal habit | Green, cubical |
| Temperature | 100 K |
| Wavelength | 0.7107 A |
| Crystal system, space group | Rhombohedral, R-3 |
| Unit cell dimensions | a = 28.620(4) Å alpha = 90 deg. |
| | b = 28.620(4) Å beta = 90 deg. |
| | c = 23.355(5) Å gamma = 120 deg. |
| Volume | 16567(5) Å$^3$ |
| Z, Calculated density | 18, 1.403 Mg/m$^3$ |
| Absorption coefficient | 0.612 mm$^{-1}$ |
| F(000) | 7164 |
| Crystal size | 0.1 × 0.1 × 0.1 mm |
| Theta range for data collection | 2.98 to 26.34 deg. |
| Limiting indices | −34 ≤ h ≤ 26, −23 ≤ k ≤ 35, −20 ≤ l ≤ 29 |
| Reflections collected/unique | 18933/7461 [R(int) = 0.0426] |
| Completeness to theta = 26.37 | 99.5% |
| Absorption correction | Semi-empirical from equivalents |
| Max. and min. transmission | 1.00000 and 0.87423 |
| Refinement method | Full-matrix least-squares on F$^2$ |
| Data/restraints/parameters | 7461/0/424 |
| Goodness-of-fit on F$^2$ | 1.076 |
| Final R indices [I > 2sigma(I)] | R1 = 0.0662, wR2 = 0.1875 |
| R indices (all data) | R1 = 0.1032, wR2 = 0.2081 |
| Largest diff. peak and hole | 2.722 and −0.626 e.A$^{-3}$ |

Example 17

Catalyst E, [RuCl$_2$(=CH(o-CH(Me)CONH$_2$)Ph)(ImH$_2$Mes)]

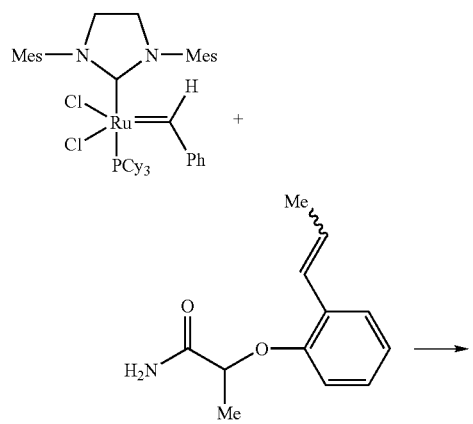

A suspension of 1.00 g (1.19 mmol) of [RuCl$_2$(PCy$_3$)(ImH$_2$Mes)(phenylmethylene)] (commercially available from Sigma-Aldrich Inc., St. Louis, USA), 0.15 g (1.47 mmol) of copper chloride and 0.30 g (1.47 mmol) of 2-[((E, Z)-2-propenyl)-phenoxy]-propionamide as a 3.5:1 mixture of E/Z-isomers in 75 mL of dichloromethane was stirred for 30 min at 40° C. The reaction mixture was evaporated to dryness at 40° C./10 mbar. The crude title product was dissolved in 100 mL of ethyl acetate and the formed suspension filtered. The filtrate was evaporated to dryness at 40° C./10 mbar. The crude title product was purified by repeated digestion with pentane/THF to yield 0.41 g (53%) of the title compound as a green solid. MS: 655.1 (M$^+$). Anal. calcd. for C$_{31}$H$_{37}$Cl$_2$N$_3$O$_2$Ru: C, 56.79; H, 5.69; N, 6.41; Cl, 10.81. Found: C, 56.23; H, 5.59; N, 6.16; Cl, 10.84.

Crystals of the title compound suitable for X-ray crystal structure analysis were grown by vapor diffusion of pentane into a solution of 10 mg of [RuCl$_2$(=CH(o-OCH(Me)CONH$_2$) Ph)(ImH$_2$Mes)] in 0.5 mL of tetrahydrofuran at room temperature.

Figure 3:
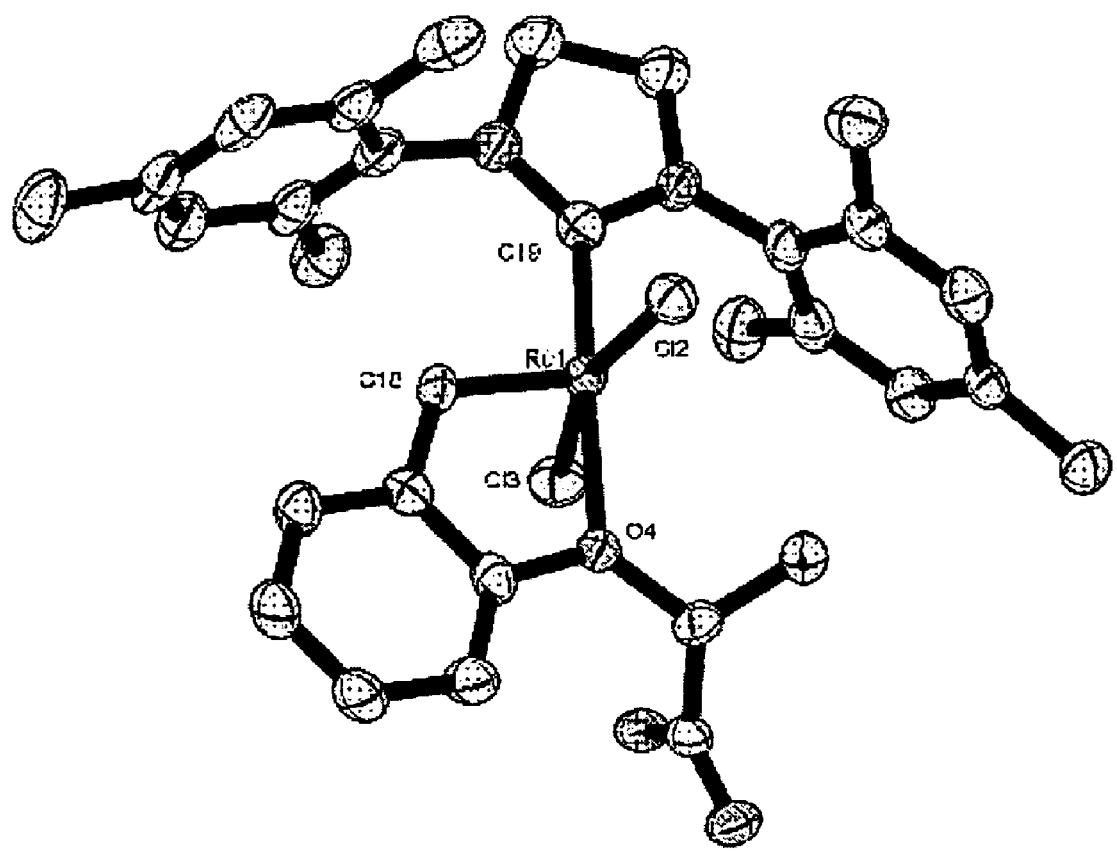
FIG. 3 is an Ortep plot of RuCl$_2$(=CH(o-OCH(Me)CONH$_2$)Ph)(ImH$_2$Mes) (formula E). The collection and the refinement of parameters for the crystallographic analysis are summarized in Table X5 and representative bond lengths and bond angles are reported in Table X6 in the examples section.

FIG. 3 shows a labeled view of the complex of formula E.

TABLE X5

Crystal data and structure refinement for complex E

| | |
|---|---|
| Empirical formula | C$_{33}$H$_{37}$Cl$_2$N$_3$O$_2$Ru |
| Formula weight | 687.63 |
| Crystal habit | Green, plates |
| Temperature | 100 K |
| Wavelength | 0.7107 Å |
| Crystal system, space group | Monoclinic, C2/c |
| Unit cell dimensions | a = 31.8797(11) Å alpha = 90 deg.. |
| | b = 15.8204(4) Å beta = 110.956(3)deg.. |
| | c = 16.6158(5) Å gamma = 90 deg |
| Volume | 7825.9(4) Å$^3$ |
| Z, Calculated density | 8, 1.167 Mg/m$^3$ |
| Absorption coefficient | 0.566 mm$^{-1}$ |
| F(000) | 2832 |
| Crystal size | 0.2 × 0.1 × 0.05 mm |
| Theta range for data collection | 2.98 to 26.02 deg. |
| Limiting indices | −39 ≦ h ≦ 39, −19 ≦ k ≦ 19, −20 ≦ l ≦ 16 |
| Reflections collected/unique | 22018/7675 [R(int) = 0.1382] |
| Completeness to theta = 26.37 | 99.5% |
| Absorption correction | None |
| Refinement method | Full-matrix least-squares on F$^2$ |
| Data/restraints/parameters | 7675/0/369 |
| Goodness-of-fit on F$^2$ | 1.103 |
| Final R indices [I > 2sigma(I)] | R1 = 0.0650, wR2 = 0.1988 |
| R indices (all data) | R1 = 0.1050, wR2 = 0.2223 |
| Largest diff. peak and hole | 1.946 and −0.879 e. Å$^{-3}$ |

-continued

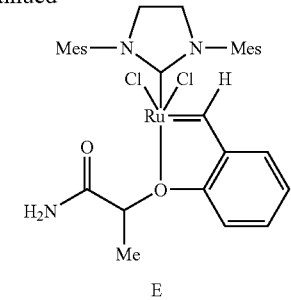

E

TABLE X6

Selected Bond Lengths (Å) and Angles (deg) for Complex E

| Bond Lengths (Å) | |
|---|---|
| Ru(1) C(18) | 1.839(5) |
| Ru(1) C(19) | 1.970(6) |
| Ru(1) O(4) | 2.257(4) |
| Ru(1) Cl(2) | 2.3371(15) |
| Ru(1) Cl(3) | 2.3415(15) |
| Bond Angles (deg) | |
| C(18)-Ru(1)-C(19) | 103.1(3) |
| C(18)-Ru(1)-O(4) | 79.6(2) |
| C(19)-Ru(1)-O(4) | 177.19(18) |
| C(18)-Ru(1)-Cl(2) | 96.61(19) |
| C(19)-Ru(1)-Cl(2) | 93.01(17) |

TABLE X6-continued

Selected Bond Lengths (Å) and Angles (deg) for Complex E

| | |
|---|---|
| O(4)-Ru(1)-Cl(2) | 87.38(11) |
| O(4)-Ru(1)-Cl(3) | 85.21(11) |
| Cl(2)-Ru(1)-Cl(3) | 161.50(6) |

Example 18

Catalyst No. G, [RuCl$_2$(=CH(o-OCH(Me)CON-HPh)Ph)(ImH$_2$Mes)]

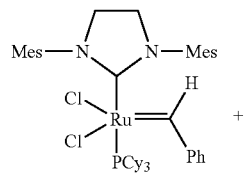

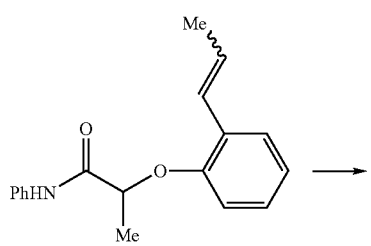

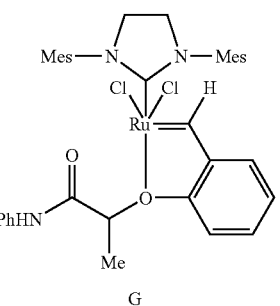

A suspension of 1.00 g (1.18 mmol) of [RuCl$_2$(PCy$_3$)(ImH$_2$Mes)(phenylmethylene)] (commercially available from Sigma-Aldrich Inc., St. Louis, USA), 0.13 g (1.30 mmol) of copper chloride and 0.38 g (1.30 mmol) of N-phenyl-2-[((E,Z)-2-propenyl)-phenoxy]-propionamide as a 4:1 mixture of E/Z-isomers in 75 mL of dichloromethane was stirred for 30 min at 40° C. The reaction mixture was evaporated to dryness at 40° C./10 mbar. The residue was stirred in 75 mL of ethyl acetate for 30 min at room temperature. The dark green suspension was filtered and the filtrate was evaporated to dryness at 40° C./10 mbar. The crude title product was purified by silica gel chromatography (cyclohexane/ethyl acetate 4:1) to yield 0.75 g (88% yield) of the title compound as a green powder.

MS: 731.1 (M$^+$). Anal. calcd. for C$_{37}$H$_{41}$Cl$_2$N$_3$O$_2$Ru.⅓ C$_6$H$_{12}$: C, 61.65; H, 5.97; N, 5.53; Cl, 9.33. Found: C, 61.83; H, 6.71; N, 5.35; Cl, 8.93.

Example 19

Catalyst No. J, [RuCl$_2$(=CH(o-OCH(Me)CO—N-Pyrrolidine)Ph)(ImH$_2$Mes)]

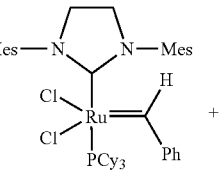

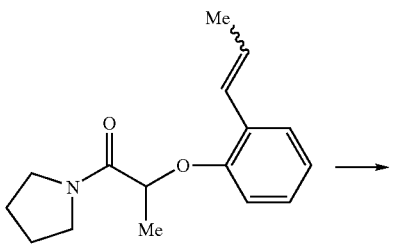

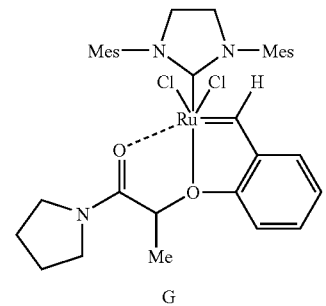

A suspension of 1.00 g (1.18 mmol) of [RuCl$_2$(PCy$_3$)(ImH$_2$Mes)(phenylmethylene)] (commercially available from Sigma-Aldrich Inc., St. Louis, USA), 0.13 g (1.30 mmol) of copper chloride and 0.36 g (1.30 mmol) of 2-[((E,Z)-2-propenyl)-phenoxy]-1-pyrrolidine-1-yl-propan-1-one as a 4:1 mixture of E/Z-isomers in 75 mL of dichloromethane was stirred for 30 min at 40° C. The reaction mixture was evaporated to dryness at 40° C./10 mbar. The residue was stirred in 60 mL of ethyl acetate for 30 min at room temperature. The dark green suspension was filtered and the filtrate was evaporated to dryness at 40° C./10 mbar. The crude title product was purified by silica gel chromatography (dichloromethane/methanol 98:2) to yield 0.52 g (62% yield) of the title compound as a green powder. MS: 709.2 (M$^+$). Anal.

calcd. for $C_{35}H_{43}Cl_2N_3O_2Ru \cdot 0.85CH_2Cl_2$: C, 55.04; H, 5.76; N, 5.37, Cl 16.83. Found: C, 54.52; H, 5.74; N, 5.29, Cl 16.82.

Example 20

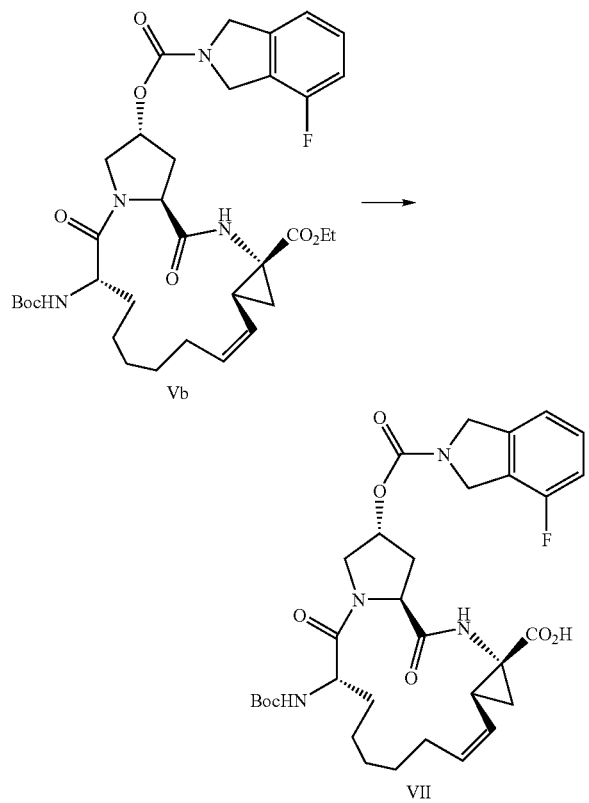

Preparation of (2R,6S,12Z,13aS,14aR,16aS)-6-[[(tert-butoxy)carbonyl]amino]-2-[[(4-fluoro-1,3-dihydro-2H-isoindol-2-yl)carbonyl]oxy]-1,2,3,6,7,8,9,10,11,13a,14,15,16,16a-hexadecahydro-5,16-dioxo]-cyclopropa[e]pyrrolo[1,2-a][1,4]diazacyclopentadecine-14a(5H)-carboxylic acid To a solution of 59.7 g (90.9 mmol) of RCM-ester Vb in 350 g of ethanol was added within one hour at 7° C. 231 g of a sodium hydroxide solution (20% in water) and the resulting mixture was stirred for 6 hours at 5-10° C. The mixture was then treated at 10° C. with 110 g of concentrated hydrochloric acid (37%). From the resulting mixture (approx. 800 mL) ethanol/water was distilled off until a residual volume of 350-400 mL was obtained in the reactor. The residue was treated at 40° C. with 320 g of dichloromethane and 55 g of water and the resulting biphasic mixture was stirred at 40° C. for 20 minutes. Stirring was stopped and the layers were allowed to separate for 15 minutes. The lower organic layer was separated. The aqueous layer was extracted with 64 g of dichloromethane and the combined organic layers were washed with water (1×55 g). From the organic layer dichloromethane was distilled off at atmospheric pressure and the removed solvent was continuously replaced by tetrahydrofuran; whereby the product crystallized out. In total, 600 g of tetrahydrofuran have been added. At the end of the distillation a volume of approx. 700 mL was adjusted in the reactor. After the distillation the suspension was heated to reflux for 5 hours. The suspension was then cooled to 0° C. within 2 hours and stirred at this temperature for additional 3 hours. The crystals were filtered off, washed with 95 g of tetrahydrofuran and dried at 50° C./<30 mbar for 10 hours to afford 55.20 g (87% corrected yield) of the title compound as white crystals with a purity of 98.4% (area), an assay of 90.2% (m/m) and a THF content of 8.5%.

MS: 627.3 ($M^+$-H); $^1$H-NMR (400 Miz, DMSO-$d_6$): 12.2 (s, 1H), 8.73-8.66 (m, 1H), 7.39-7.31 (m, 1H), 7.22-7.02 (m, 3H), 5.57-5.46 (m, 1H), 5.31-5.21 (m, 2H), 4.67 (s, br, 4H), 4.47-4.38 (m, 1H), 4.29-4.20 (m, 1H), 3.98-3.88 (m, 1H), 3.71-3.62 (m, 1H), 2.70-2.55 (m, 1H), 2.29-2.08 (m, 3H), 1.75-1.0 (m, 11H), 1.10 and 1.07 (2s, 9H).

Example 21

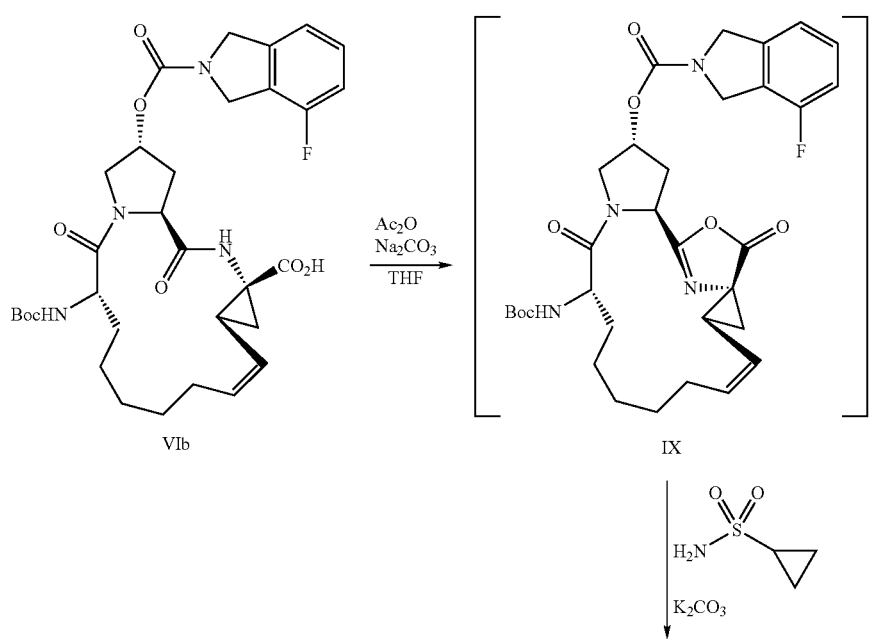

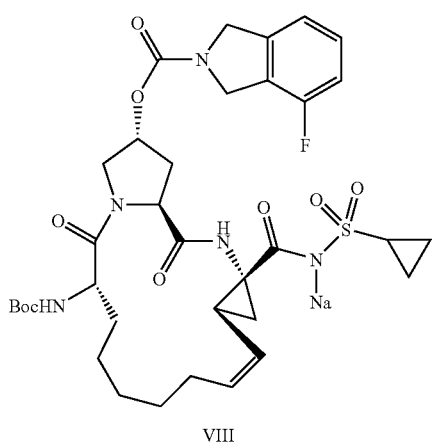

VIII

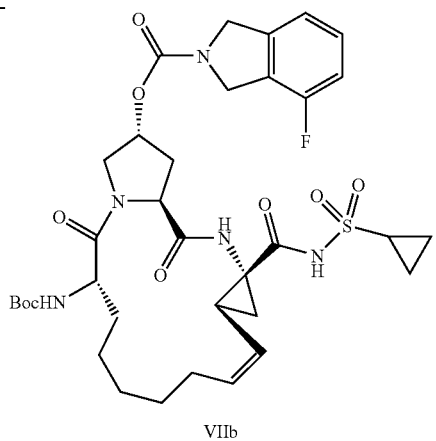

VIIb

Preparation of Sodium ((2R,6S,13aS,14aR,16aS,Z)-6-(tert-butoxycarbonylamino)-2-(4-fluoroisoiindoline-2-carbonyloxy)-5,16-dioxo-1,2,3,5,6,7,8,9,10,11,13a,15,16a-hexadecahydrocyclopropa[e]pyrrolo[1,2-a][1,4]diazacyclopentadecine-14a-carbonyl)(cyclopropylsulfonyl)amide (HCV protease inhibitor; compound VIII)

To a suspension of 30.0 g (0.043 mol) of carboxylic acid (product of example 20 with an assay of 90.2% (m/m)) and 14.0 g of sodium carbonate in 225 g of tetrahydrofuran was added at 45° C. within 30 minutes 7.60 g (0.074 mol) of acetic acid anhydride and the resulting mixture was stirred at 45° C. for 8 hours. To the resulting suspension was then added 30.2 g (0.17 mol) of potassium carbonate and 8.0 g (0.065 mol) of cyclopropyl-sulfonamide. The mixture was heated to 62° C. and stirred at this temperature for 17 hours. The mixture was concentrated to a residual volume of 200 mL and then treated with 200 g of water. The biphasic mixture was stirred for 15 minutes and the layers were then allowed to separate. The lower aqueous phase was removed. The organic phase was diluted with 90 g of ethyl acetate and washed with 3% sulfuric acid (1×140 g) and water (3×130 g). The organic layer was concentrated to dryness and then diluted with 400 mL of ethyl acetate. Residual amounts of water were removed by a continuous azeotropic distillation with ethyl acetate. The mixture was then treated at 110° C. with 20 mL of methanol, followed by 10.0 g of sodium methylate (30% in methanol). From the resulting mixture approx. 300 mL of ethyl acetate/methanol were then distilled off. The mixture was then treated at 34° C. within one hour with 300 mL of ethyl acetate and 5 g of water. The resulting mixture was allowed to cool to ambient temperature within 4 hours. The crystals were filtered off, washed with 80 mL of ethyl acetate and dried at 80° C./<30 mbar for 20 hours to afford 30.4 g (87% corrected yield) of the title compound as white crystals with an assay of 92.7% (m/m).

MS: 732.28 (M$^+$+H), 676.23, 632.25. $^1$H-NMR (400 MHz, DMSO-d): 7.89-7.80 (m, 1H), 7.39-7.31 (m, 1H), 7.21-7.06 (m, 2H), 6.97-6.90 (m, 1H), 5.49-4.41 (m, 1H), 5.31-5.21 (m, 2H), 4.66 (s, br, 4H), 4.45-4.35 (m, 1H), 4.19-4.08 (m, 2H), 3.91-3.81 (m, 1H), 2.68-2.58 (m, 1H), 2.30-2.14 (m, 3H), 2.0-1.2 (m, 12H), 1.17 and 1.14 (2s, 9H), 0.78-0.69 (m, 2H), 0.62-0.53 (m, 2H).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound according to formula I:

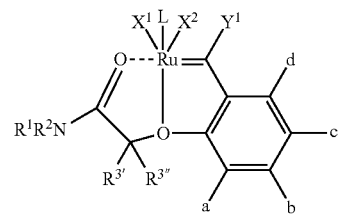

I wherein the dotted line signifies an optional bond;
L is a neutral ligand;
$X^1$ and $X^2$ independently of each other are anionic ligands;
$Y^1$ is hydrogen, $C_{1-6}$-alkyl, $C_{3-8}$-cycloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, aryloxy, $C_{1-6}$-alkoxycarbonyl, $C_{1-6}$-alkylthio, aryl, arylthio, $C_{1-6}$-alkylsulfonyl, $C_{1-6}$-alkylsulfinyl;
a, b, c and d are independently selected from hydrogen, $C_{1-6}$-alkyl, halogen-$C_{1-6}$-alkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl-or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, $SO_3$-$C_{1-6}$-alkyl, OSi($C_{1-6}$-alkyl)$_3$ or $SO_2$—NR'R" wherein R' and R" are independently hydrogen, aryl, $C_{1-6}$-alkyl or R' and R" together with the N atom to which they are attached form a carbocycle;

R$^1$ and R$^2$ are independently hydrogen, C$_{1-6}$-alkyl, C$_{3-8}$-cycloalkyl, aryl or aryl-C$_{1-6}$-alkyl; or, R$^1$ and R$^2$ together with the N atom to which they are attached form a 5 to 8 member carbocycle which optionally contain a nitrogen, oxygen or sulfur as an additional hetero atom;

R$^{3'}$ and R$^{3''}$ are independently hydrogen, C$_{1-6}$-alkyl, C$_{3-8}$-cycloalkyl, aryl, aryl-C$_{1-6}$-alkyl.

2. A compound according to claim 1 wherein the dotted line signifies a bond resulting in a hexacoordinated Ru (II) complex.

3. A compound according to claim 1 wherein:
L is IIa, IIb, IIc or IIf;

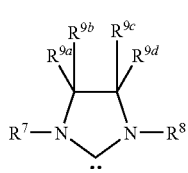

IIa

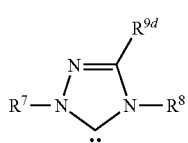

IIb

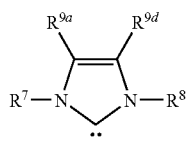

IIc

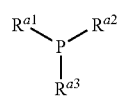

IIf wherein R$^7$ and R$^8$ are independently C$_{1-6}$-alkyl, aryl, C$_{2-6}$-alkenyl or 1-adamantyl and R$^{9a}$, R$^{9b}$, R$^{9c}$ and R$^{9d}$ are independently hydrogen, C$_{1-6}$-alkyl, C$_{2-6}$-alkenyl or aryl, or R$^{9b}$ and R$^{9c}$ or R$^{9a}$ and R$^{9d}$ taken together form a -(CH$_2$)$_4$-bridge;

or, when L is IIc R$^{9a}$ and R$^{9d}$ can both be halogen;

or, when L is IIf, R$^{a1}$, R$^{a2}$ and R$^{a3}$ are independently C$_{1-6}$ alkyl, C$_{3-8}$ cycloalkyl, aryl, heteroaryl, or R$^{a1}$ and R$^{a2}$, or R$^{a2}$ and R$^{a3}$ or R$^{a1}$ and R$^{a3}$ taken together form a 1,5-bridged cycloalkyl group.

4. A compound according to claim 3 wherein L is IId or IIe:

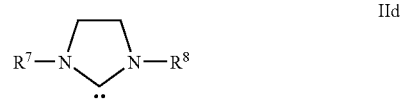

IId

IIe wherein R$^7$ and R$^8$ are independently C$_{1-6}$-alkyl, , 1-adamantyl, phenyl which is di- or tri-substituted with C$_{1-6}$ alkyl or naphthyl which is di- or tri-substituted with C$_{1-6}$ alkyl and Ru (II) complex is hexacoordinated.

5. A compound according to claim 4 wherein R$^7$ and R$^8$ are 2, 4, 6-trimethylphenyl or 2,7-di-isopropyl-naphthyl.

6. A compound according to claim 2, wherein X$^1$ and X$^2$ are independently halogen.

7. A compound according to claim 6, wherein X$^1$ and X$^2$ are chloro.

8. A compound according to claim 2 wherein Y$^1$ is hydrogen.

9. A compound according to claim 2 wherein a, b and d are hydrogen.

10. A compound according to claim 2 wherein c is hydrogen, halogen, nitro, C$_{1-6}$-alkylcarbonyl amino, aryl carbonyl amino, aryl sulfonyl amino, alkyl sulfonyl amino, halogen-C$_{1-6}$-alkyl sulfonyl amino, SO$_2$—NR'R'' wherein R' and R' are independently hydrogen, C$_{1-6}$-alkyl, aryl or R' and R'' together with the N atom to which they are attached form a carbocycle.

11. A compound according to claim 2 wherein R$^1$ and R$^2$ are independently hydrogen or C$_{1-6}$-alkyl or R$^1$ and R$^2$ together with the N atom to which they are attached form a 6 member carbocycle which contains oxygen as additional hetero atom.

12. A compound according to claim 2 wherein R$^{3'}$ and R$^{3''}$ are independently hydrogen or C$_{1-6}$-alkyl.

13. A compound according to claim 1 selected from

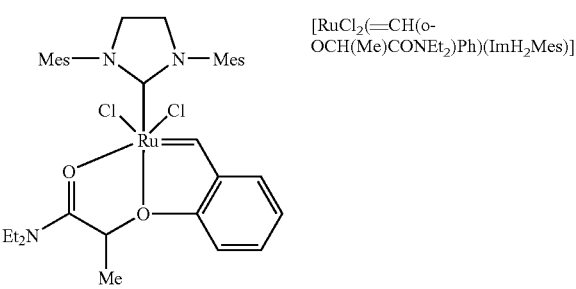

[RuCl$_2$(=CH(o-OCH(Me)CONEt$_2$)Ph)(ImH$_2$Mes)]

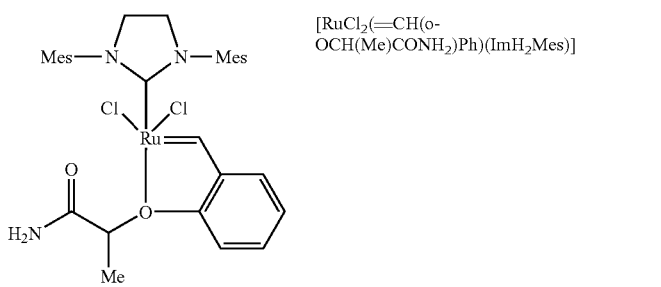
[RuCl$_2$(=CH(o-OCH(Me)CONH$_2$)Ph)(ImH$_2$Mes)]
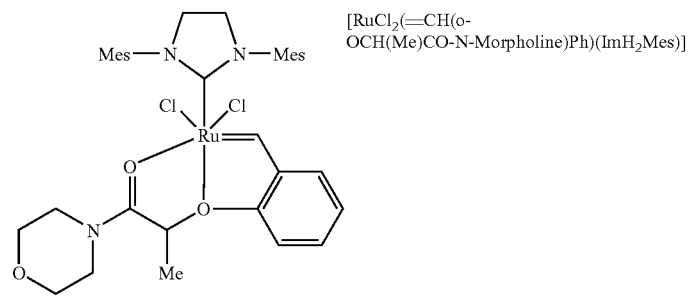
[RuCl$_2$(=CH(o-OCH(Me)CO-N-Morpholine)Ph)(ImH$_2$Mes)]
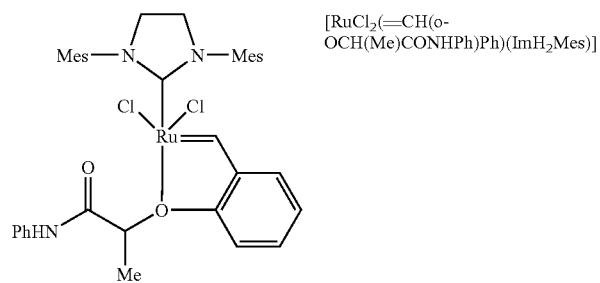
[RuCl$_2$(=CH(o-OCH(Me)CONHPh)Ph)(ImH$_2$Mes)]
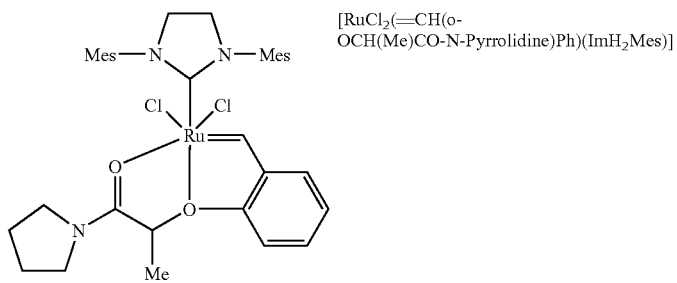
[RuCl$_2$(=CH(o-OCH(Me)CO-N-Pyrrolidine)Ph)(ImH$_2$Mes)]
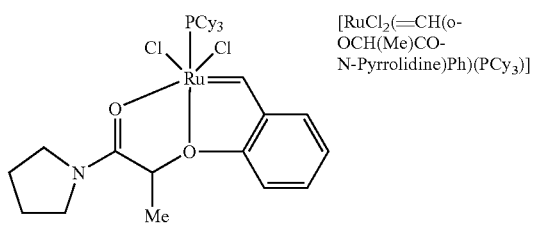
[RuCl$_2$(=CH(o-OCH(Me)CO-N-Pyrrolidine)Ph)(PCy$_3$)]

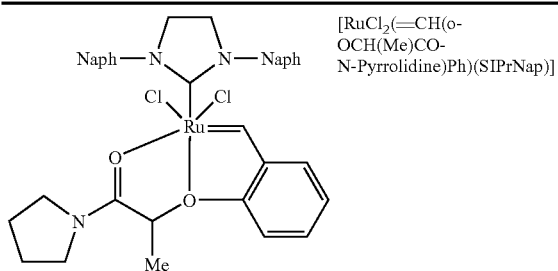

[RuCl$_2$(=CH(o-OCH(Me)CO-N-Pyrrolidine)Ph)(SIPrNap)]

Naph = 2,7-di-iso-propyl-naphthalen-1-yl

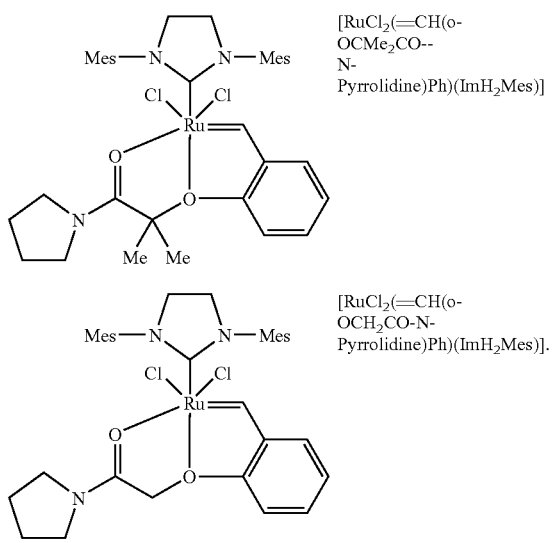

[RuCl$_2$(=CH(o-OCMe$_2$CO-- N-Pyrrolidine)Ph)(ImH$_2$Mes)]

[RuCl$_2$(=CH(o-OCH$_2$CO-N-Pyrrolidine)Ph)(ImH$_2$Mes)].

14. A process for the preparation of a compound according to claim 1 which process comprises contacting a compound according to formula 1a with a Ru-complex

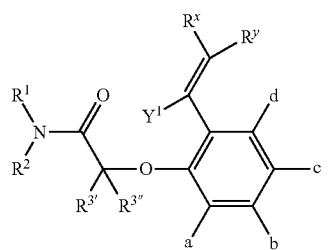 1.1

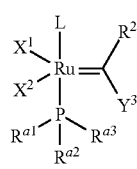 2.1

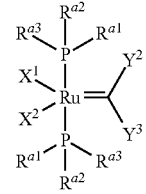 2.2 of formula 2.1 or 2.2 wherein: L is IIa, IIb,IIc;

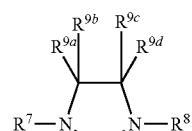 IIa

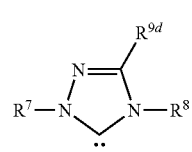 IIb

-continued

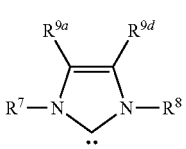
IIc $X^1$ and $X^2$ independently of each other are anionic ligands;
$Y^2$ and $Y^3$ independently of each other are hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl, $C_{1-6}$-alkylsulfinyl, or,
$Y^2$ and $Y^3$ taken together form a cycle of the type wherein G is hydrogen or aryl; or,

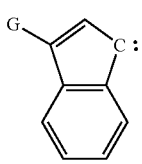
3a $Y^2$ and $Y^3$ together form a cumulenyl group of formula 3b or 3c;

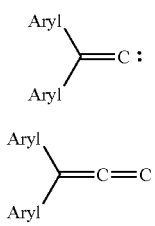

$R^{a1}$, $R^{a2}$ and $R^{a3}$ independently of each other are $C_{1-6}$-alkyl, $C_{3-8}$-cycloalkyl, aryl, heteroaryl or $R^{a1}$ and $R^{a2}$ or $R^{a2}$ and $R^{a3}$ or $R^{a1}$ and $R^{a3}$ form together a 1,5-bridged cyclooctyl group; and,
$R^x$ and $R^y$ are independently hydrogen, $C_{1-6}$ alkyl optionally substituted by one or mor halogen atoms or aryl substituted by one or more halogen atoms or $C_{1-6}$ alkyl.

15. A process according to claim 14 wherein 1.1 is contacted with 2.1 or 2.2 in an inert solvent at a temperature between 0° C. and 80° C.

16. A process according to claim 15 wherein 1.1 is contacted with 2.1 or 2.2 in the presence of CuCl.

17. A compound of formula 1a

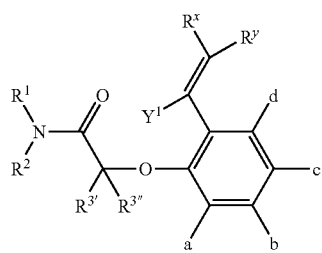
1a wherein:
$R^1$ and $R^2$ are independently hydrogen, $C_{1-6}$-alkyl, $C_{3-8}$-cycloalkyl, aryl or aryl-$C_{1-6}$-alkyl; or, $R^1$ and $R^2$ together with the N atom to which they are attached form a 5 to 8 member carbocycle which optionally contain a nitrogen, oxygen or sulfur as an additional hetero atom with the proviso that when $R^1$ and $R^2$ are H at least one of $R^{3'}$, $R^{3''}$, $R^x$ or $R^y$ is other than hydrogen;

$R^{3'}$ and $R^{3''}$ are independently hydrogen, $C_{1-6}$-alkyl, $C_{3-8}$-cycloalkyl, aryl-$C_{1-6}$-alkyl;

$Y^1$ is hydrogen, $C_{1-6}$-alkyl, $C_{3-8}$-cycloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, aryloxy, $C_{1-6}$-alkoxycarbonyl, $C_{1-6}$-alkylthio, arylthio, $C_{1-6}$-alkylsulfonyl, $C_{1-6}$-alkylsulfinyl;

a, b, c and d are independently selected from hydrogen, $C_{1-6}$-alkyl, halogen-$C_{1-6}$-alkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl-or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, $SO_3$—$C_{1-6}$-alkyl, $OSi(C_{1-6}$-alkyl)$_3$ or $SO_2$—NR'R" wherein R' and R" are independently hydrogen, aryl, $C_{1-6}$-alkyl or R' and R" together with the N atom to which they are attached form a carbocycle;

$R^x$ and $R^y$ independently of each denote hydrogen, $C_{1-6}$-alkyl optionally substituted by one or more halogen atoms or aryl optionally substituted by one or more halogen atoms or by $C_{1-6}$-alkyl.

18. A compound according to claim 17 which compound is selected from the group consisting of 1a, 1b, 1c, 1d, 1e, 1f, 1g and 1h:

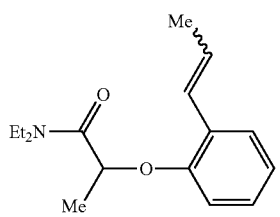
1a

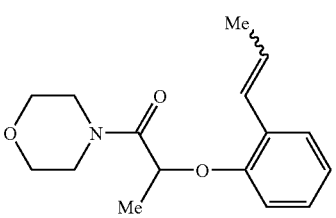
1b

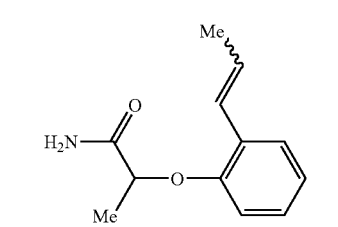
1c

-continued

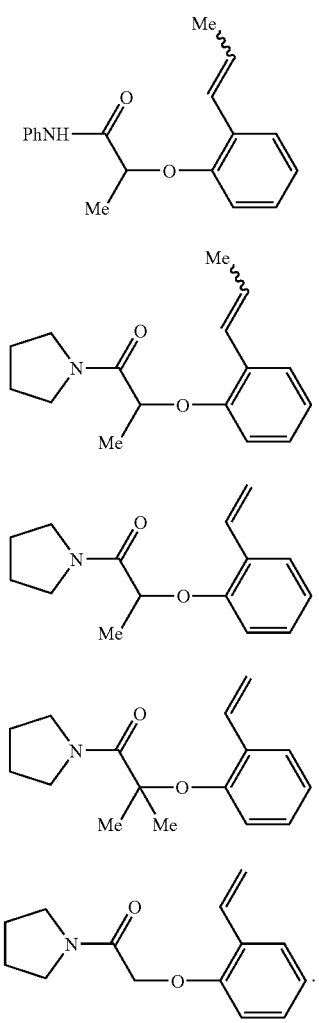

1d
1e
1f
1g
1h

19. A process for the manufacture of a macrocyclic compound of formula III

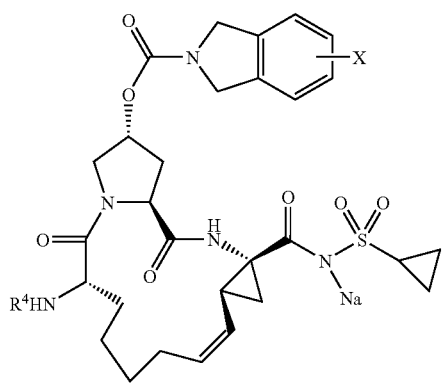

III wherein $R^4$ is an amino protecting group and X is a halogen atom, comprising the step of subjecting a diene compound of formula IV to form a macrocyclic ester of the formula V wherein:

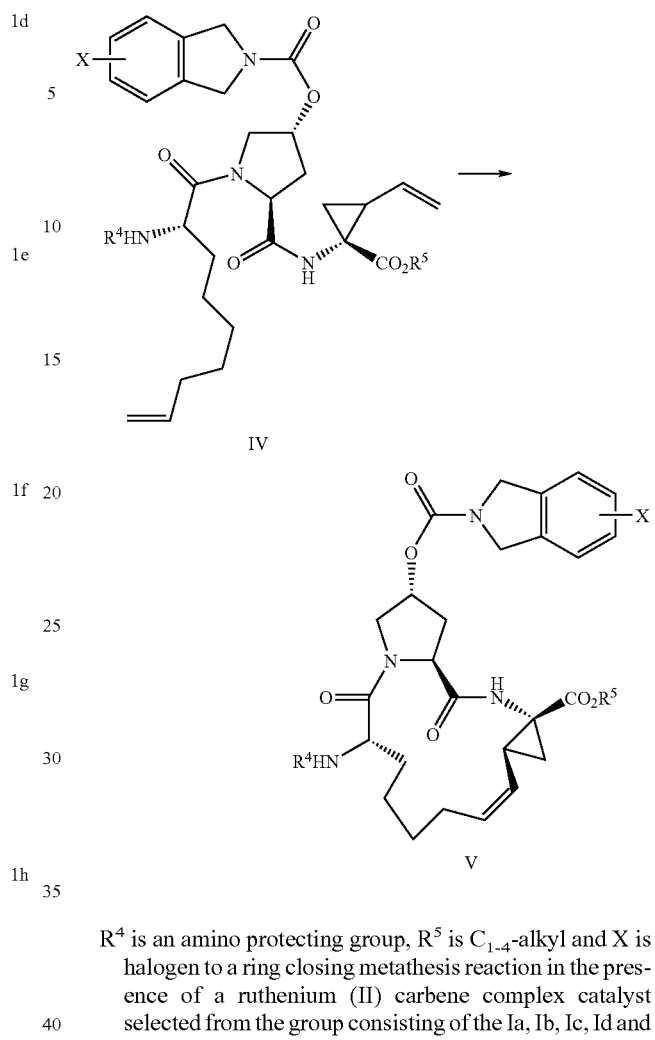

IV

V $R^4$ is an amino protecting group, $R^5$ is $C_{1-4}$-alkyl and X is halogen to a ring closing metathesis reaction in the presence of a ruthenium (II) carbene complex catalyst selected from the group consisting of the Ia, Ib, Ic, Id and Ie, wherein:

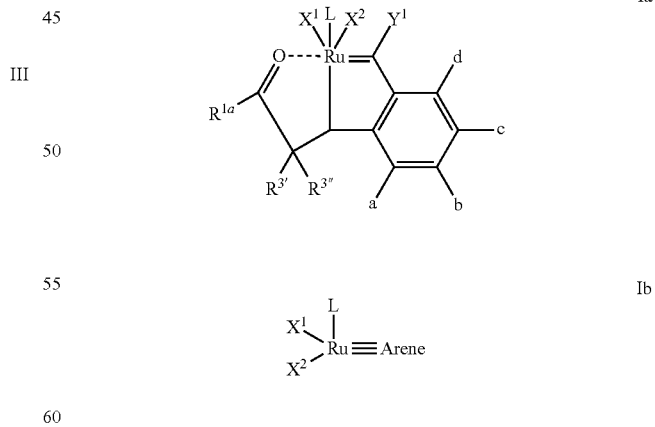

Ia

Ib

Ic

-continued

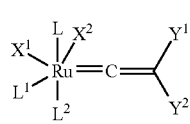
Id

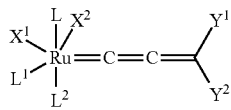
Ie the dotted line represents an optional bond;

L, $L^1$ and $L^2$ are neutral ligands;

$X^1$ and $X^2$ are independently anionic ligands;

$Y^1$ and $Y^2$ are independently hydrogen, $C_{1-6}$-alkyl, $C_{3-8}$-cycloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, aryloxy, $C_{1-6}$-alkoxycarbonyl, $C_{1-6}$-alkylthio, aryl, arylthio, $C_{1-6}$-alkylsulfonyl or $C_{1-6}$-alkylsulfinyl;

a, b, c and d are independently hydrogen, $C_{1-6}$-alkyl, halogen-$C_{1-6}$-alkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono -$C_{1-6}$-alkyl-or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, $SO_3$—$C_{1-6}$-alkyl, $OSi(C_{1-6}$-alkyl$)_3$ or $SO_2$—NR'R'' wherein R' and R'' are independently hydrogen, aryl or $C_{1-6}$-alkyl or R' and R'' together with the N atom to which they are attached form a carbocycle;

Arene stands for phenyl or naphthyl optionally substituted by one or more substituents selected from the group consisting of halogen, hydroxy, cyano, halogen-$C_{1-6}$-alkyl, $NO_2$, amino, mono-$C_{1-6}$-alkyl-or di-$C_{1-6}$-alkylamino, carboxy, aminocarbonyl, $C_{1-6}$-alkyl, $C_{1-6}$-alkylcarbonyl, $C_{1-6}$-alkylsulfonyl, aryl, aryloxy $SO_2$-aryl, $SO_3H$, $SO_3$—$C_{1-6}$-alkyl and $SO_2$—NR'R''wherein R' and R'' are independently hydrogen or $C_{1-6}$-alkyl;

$R^{1a}$ is hydrogen, hydroxy, $C_{1-6}$-alkoxy, $C_{2-6}$-alkenyloxy, $C_{3-8}$-cycloalkyloxy, halogen, $C_{1-6}$-alkyloxy, aryloxy, $C_{1-6}$-alkylthio, arylthio, or —NR'R'' wherein R' and R'' are independently hydrogen, $C_{1-6}$-alkyl, $C_{3-8}$-cycloalkyl, aryl, aryl-$C_{1-6}$-alkyl or wherein R' and R'' together with the N atom to which they are attached form a 5 to 8 member carbocycle optionally containing a nitrogen, oxygen or sulfur hetero atom;

$R^{3'}$ and $R^{3''}$ are independently hydrogen, $C_{1-6}$-alkyl, $C_{3-8}$-cycloalkyl, aryl or $C_{7-18}$-arylalkyl; or, $R^{1a}$ and $R^{3'}$ together form a 5 to 12 member carbocycle.

20. A process according to claim 19 which process further comprises the steps of:

b) hydrolyzing the macrocyclic ester of formula V in the presence of a base to form the macrocyclic acid of the formula VI

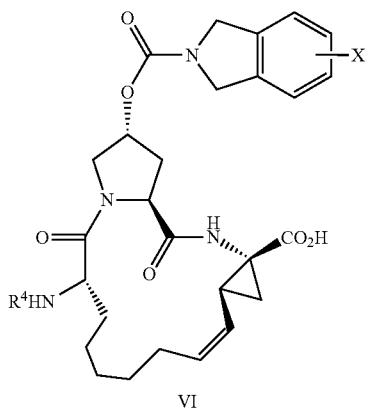
VI wherein $R^4$ is an amino protecting group and X is halogen;

c) contacting VI with cyclopropylsulfonamide to form the macrocyclic sulfonamide of formula VII by coupling the macrocyclic acid of formula VI with cyclopropyl sulphonamide; and,

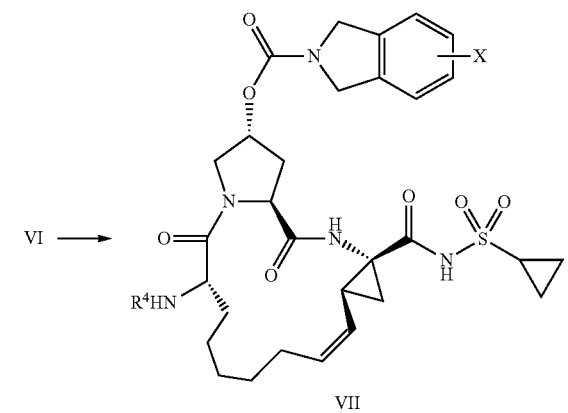
VII wherein $R^4$ is an amino protecting group and X is halogen d) treating the macrocyclic sulfonamide of formula VII with a sodium base to form the macrocyclic compound of formula III.

21. A process according to claim 19, wherein the ruthenium (II) carbene complex catalyst is selected from compounds of the formula Ia, Ib or Ic.

22. A process according to claim 19 wherein L, $L^1$ and $L^2$ are the same or different and that at least L is a N-heterocyclic carbene ligand.

23. A process according to claim 19 wherein the ruthenium (II) carbene complex catalyst is a compound of formula Ia.

24. A process according to claim 23 wherein L is selected from IIa, IIb or IIc wherein:

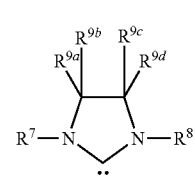
IIa

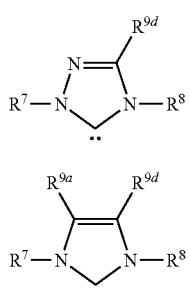

R⁷ and R⁸ are independently $C_{1-6}$-alkyl, aryl, $C_{2-6}$-alkenyl or 1-adamantyl; and, $R^{9a}$, $R^{9b}$, $R^{9c}$ and $R^{9d}$ are independently hydrogen, $C_{1-6}$-alkyl, $C_{2-6}$-alkenyl or aryl, or $R^{9b}$ and $R^{9c}$ or $R^{9a}$ and $R^{9d}$ taken together form a —$(CH_2)_4$- bridge.

25. A process according to claim 19 wherein $X^1$ and $X^2$ are independently halogen.

26. A process of claim 19 wherein the ruthenium (II) carbene complex catalyst is Ia or Ic and in each occurrence $Y^1$ and $Y^2$ are independently hydrogen, $C_{1-6}$-alkyl, aryl or arylthio.

27. A process of claim 23 wherein the ruthenium (II) carbene complex catalyst is Ia and a, b and d are hydrogen.

28. A process of claim 27 wherein c is hydrogen, halogen, nitro, $C_{1-6}$-alkylcarbonyl amino, aryl carbonyl amino, aryl sulfonyl amino, alkyl sulfonyl amino, halogen-$C_{1-6}$-alkyl sulfonyl amino, $SO_2$—NR'R" wherein R' and R" are independently hydrogen, $C_{1-6}$-alkyl or aryl or wherein R' and R" together with the N atom to which they are attached form a carbocycle.

29. A process according to claim 19 wherein the ruthenium (II) carbene complex catalyst is a compound of formula Ib and Arene is benzene, p-cymene, mesitylene or, p-xylene.

30. A process according to claim 19 wherein the ring closing metathesis reaction is performed in an organic solvent at 20° C. to 140° C.

31. A process according to claim 19 wherein the ring closing metathesis reaction is performed with a substrate to catalyst ratio in the range of 20 to 10000.

32. A process according to claim 20 wherein the hydrolysis is performed with an aqueous alkali hydroxide solution at a temperature of 0° C. to 40° C.

33. A process according to claim 20 wherein the macrocyclic acid of formula VI obtained in step (b) is isolated by way of extraction with dichloromethane and a subsequent crystallization in tetrahydrofuran.

34. A process according to claim 20 wherein the formation of the macrocyclic sulfonamide of formula VII in step (c) further comprises initially contacting the macrocyclic acid of formula VI with acetic acid anhydride in the presence of an inorganic base and a suitable organic solvent to produce the azlacton IX wherein R⁴ is an amino protecting

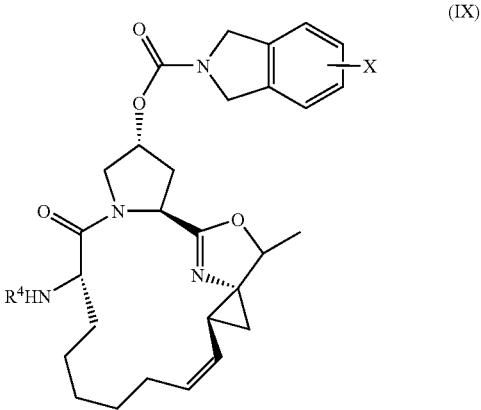

group and X is halogen and VIII with cyclopropyl sulfonamide in the presence of an inorganic base to the macrocyclic sulfonamide to afford VII.

35. A process according to claim 20 wherein the sodium base is sodium hydroxide, sodium methylate or sodium ethoxide.

36. A process according to claim 19 wherein R⁴ is Boc; $R^S$ is ethyl and the halogen substituted 2,3-dihydro-1H-isoindole moiety is 4-fluoro-2,3-dihydro-1H-isoindole.

* * * * *

UNITED STATES PATENT AND TRADEMARK OFFICE
CERTIFICATE OF CORRECTION

| | | |
|---|---|---|
| PATENT NO. | : 7,939,668 B2 | |
| APPLICATION NO. | : 12/384954 | |
| DATED | : May 10, 2011 | |
| INVENTOR(S) | : Kurt Puentener and Michelangelo Scalone | |

It is certified that error appears in the above-identified patent and that said Letters Patent is hereby corrected as shown below:

on column 55, lines 55-65 the structure should be:

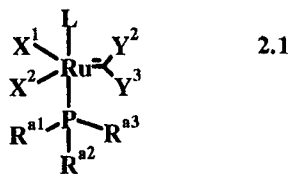

on column 60, lines 20-35 the structure should be:

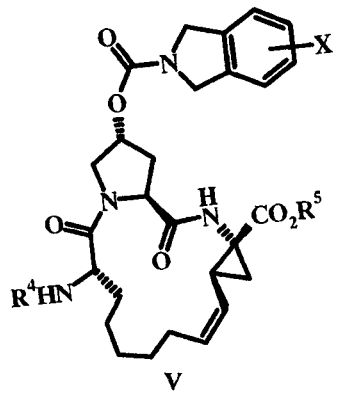

on column 60, lines 45-55 (claim 19) the structure should be:

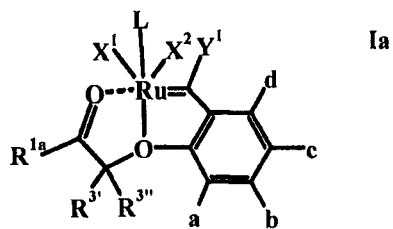

Signed and Sealed this
Twenty-eighth Day of June, 2011

David J. Kappos
*Director of the United States Patent and Trademark Office*

CERTIFICATE OF CORRECTION (continued)

on column 64, lines 15-30 (claim 34) the structure should be:

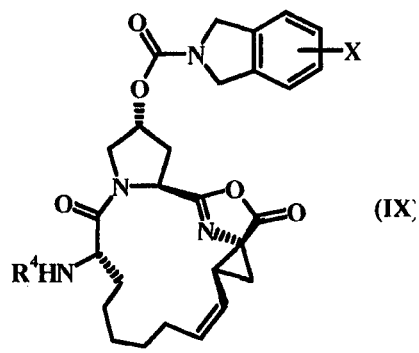

(IX)